United States Patent [19]
Franzusoff et al.

[11] Patent Number: 5,691,183
[45] Date of Patent: Nov. 25, 1997

[54] CD4+ T-LYMPHOCTYE PROTEASES AND GENES ENCODING SAID PROTEASES

[75] Inventors: Alex Franzusoff, Boulder; Luis R. Miranda, Denver, both of Colo.

[73] Assignee: University Technology Corporation, Boulder, Colo.

[21] Appl. No.: 368,852

[22] Filed: Jan. 5, 1995

Related U.S. Application Data

[63] Continuation-in-part of Ser. No. 88,322, Jul. 7, 1993, Pat. No. 5,413,914, and Ser. No. 340,185, Nov. 15, 1994, which is a continuation-in-part of Ser. No. 88,322.

[51] Int. Cl.$^6$ .................. C12N 15/57; C12N 15/74; C12N 15/81
[52] U.S. Cl. ................... 435/252.3; 435/254.2; 536/23.2
[58] Field of Search .............. 435/252.3, 254.2; 536/23.2

[56] References Cited

U.S. PATENT DOCUMENTS

| | | | |
|---|---|---|---|
| 4,929,553 | 5/1990 | Bussey et al. | 435/172.3 |
| 5,077,204 | 12/1991 | Brake et al. | 435/68.1 |
| 5,162,220 | 11/1992 | Oshima et al. | 435/224 |
| 5,225,537 | 7/1993 | Foster | 530/380 |
| 5,234,830 | 8/1993 | Oshima et al. | 435/252.3 |

FOREIGN PATENT DOCUMENTS 2024277   3/1991   Canada.

OTHER PUBLICATIONS

Angliker, "The Synthesis of Inhibitors For Processing Proteinases and Their Action on the Kex2 Proteinase of Yeast", pp. 75–81, 1993, *Biochem. J.*, vol. 293, Part 1.

Barr, "Mammalian Subtilisins: The Long–Sought Dibasic Processing Endoproteases"; pp. 1–3, 1991, *Cell*, vol. 66, Jul.

Hakes et al., "Isolation of Two Complementary Deoxyribonucleic Acid Clones from a Rat Insulinoma Cell Line Based on Similarities to Kex2 and Furin Sequences and the Specific Localization of Each Transcript to Endocrine and Neuroendocrine Tissues in Rats", pp. 3053–3063, 1991, *Endocrinology*, vol. 129, No. 6.

Kiefer et al., "Identification of a Second Human Subtilisin––Like Protease Gene in the fes/fps Region of Chromosome 15", pp. 757–769, 1991, *DNA and Cell Biol.*, vol. 10, No. 10.

Lusson et al., "cDNA Structure of the Mouse and Rat Subtilisin/kexin–Like PC5: A Candidate Proprotein Convertase Expressed in Endocrine and Nonendocrine Cells", pp. 6691–6695, 1993, *Proc. Natl. Acad. Sci. USA*, vol. 90, Jul.

Moulard et al., 1993, In *Int. Conf. AIDS*, vol. 9(1):155 (abstract No. PO–A08–0123).

Steiner et al., pp. 23435–23438, 1992, *J. Biol. Chem.*, vol. 267, No. 33.

*Primary Examiner*—Charles L. Patterson, Jr.
*Attorney, Agent, or Firm*—Sheridan Ross P.C.

[57] ABSTRACT

The present invention includes the identification and isolation of a nucleic acid molecule encoding a dibasic amino acid processing endoprotease from CD4+ T-lymphocytes as well as a protein encoded by that nucleic acid molecule. The present invention also includes related nucleic acid molecules and proteins encoded by such nucleic acid molecules as well as recombinant molecules and recombinant cells that include nucleic acid molecules of the present invention. The present invention also includes use of such nucleic acid molecules and proteins to develop therapeutic compositions that enhance or inhibit dibasic amino acid processing endoprotease activity.

27 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 483 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..483

( x i ) SEQUENCE DESCRIPTION: SEQ ID NO:1:

```
TGT  GGA  GTA  GGA  GTG  GCT  TAC  AAC  GCC  AAG  ATC  GGA  GGA  GTG  CGA  ATG        48
Cys  Gly  Val  Gly  Val  Ala  Tyr  Asn  Ala  Lys  Ile  Gly  Gly  Val  Arg  Met
 1                    5                        10                       15

CTG  GAC  GGA  GAT  GTC  ACG  GAC  ATG  GTT  GAA  GCA  AAA  TCA  GTT  AGC  TTC        96
Leu  Asp  Gly  Asp  Val  Thr  Asp  Met  Val  Glu  Ala  Lys  Ser  Val  Ser  Phe
                20                        25                       30

AAC  CCC  CAG  CAC  GTG  CAC  ATT  ACA  GCG  GCC  AGC  TGG  GGC  CCG  GAT  GAT       144
Asn  Pro  Gln  His  Val  His  Ile  Thr  Ala  Ala  Ser  Trp  Gly  Pro  Asp  Asp
           35                        40                       45

GAT  GGC  AAG  ACT  GTG  GAC  GGA  CCA  GCC  CCC  CTC  ACC  CGG  CAA  GCC  TTT       192
Asp  Gly  Lys  Thr  Val  Asp  Gly  Pro  Ala  Pro  Leu  Thr  Arg  Gln  Ala  Phe
      50                        55                       60

GAA  AAC  GGC  GTT  AGA  ATG  GGG  CGG  AGA  GGC  CTC  GGC  TCT  GTT  GTT  TGG       240
Glu  Asn  Gly  Val  Arg  Met  Gly  Arg  Arg  Gly  Leu  Gly  Ser  Val  Val  Trp
 65                        70                       75                       80

GCA  TCT  GGA  AAT  GGT  GGA  AGG  AGC  AAA  GAC  CAC  TGC  TCC  TGT  GAT  GGC       288
Ala  Ser  Gly  Asn  Gly  Gly  Arg  Ser  Lys  Asp  His  Cys  Ser  Cys  Asp  Gly
                85                        90                       95

TAC  ACC  AAC  AGC  ATC  TAC  ACC  ATC  TCC  ATC  AGC  AGC  ACT  GCA  GAA  AGC       336
Tyr  Thr  Asn  Ser  Ile  Tyr  Thr  Ile  Ser  Ile  Ser  Ser  Thr  Ala  Glu  Ser
          100                       105                      110

GGA  AAG  GAA  CCT  TGG  TAC  CTG  GAA  GAG  TGT  TCA  TCC  ACG  CTG  GCC  ACA       384
Gly  Lys  Glu  Pro  Trp  Tyr  Leu  Glu  Glu  Cys  Ser  Ser  Thr  Leu  Ala  Thr
     115                       120                      125

ACC  TAC  AGC  AGC  GGG  GAG  TCC  TAC  GAT  AAG  AAA  ATC  ATC  ACT  ACA  GAT       432
Thr  Tyr  Ser  Ser  Gly  Glu  Ser  Tyr  Asp  Lys  Lys  Ile  Ile  Thr  Thr  Asp
     130                       135                      140

CTG  AGG  CAG  CGT  TGC  ACG  GAC  AAC  CAC  TCA  GGC  ACC  TCA  GCC  TCT  GCT       480
Leu  Arg  Gln  Arg  Cys  Thr  Asp  Asn  His  Ser  Gly  Thr  Ser  Ala  Ser  Ala
145                       150                      155                      160

CCC                                                                                 483
Pro
```

( 2 ) INFORMATION FOR SEQ ID NO:2:

( i ) SEQUENCE CHARACTERISTICS:
        ( A ) LENGTH: 161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Cys  Gly  Val  Gly  Val  Ala  Tyr  Asn  Ala  Lys  Ile  Gly  Gly  Val  Arg  Met
```

```
 1               5                    10                   15
Leu Asp Gly Asp Val Thr Asp Met Val Glu Ala Lys Ser Val Ser Phe
            20                  25                30

Asn Pro Gln His Val His Ile Thr Ala Ala Ser Trp Gly Pro Asp Asp
        35              40                  45

Asp Gly Lys Thr Val Asp Gly Pro Ala Pro Leu Thr Arg Gln Ala Phe
    50              55                      60

Glu Asn Gly Val Arg Met Gly Arg Arg Gly Leu Gly Ser Val Val Trp
65              70                      75                      80

Ala Ser Gly Asn Gly Gly Arg Ser Lys Asp His Cys Ser Cys Asp Gly
                85                  90                  95

Tyr Thr Asn Ser Ile Tyr Thr Ile Ser Ile Ser Ser Thr Ala Glu Ser
            100             105                 110

Gly Lys Glu Pro Trp Tyr Leu Glu Glu Cys Ser Ser Thr Leu Ala Thr
        115                 120                 125

Thr Tyr Ser Ser Gly Glu Ser Tyr Asp Lys Lys Ile Ile Thr Thr Asp
    130                 135                 140

Leu Arg Gln Arg Cys Thr Asp Asn His Ser Gly Thr Ser Ala Ser Ala
145                 150                 155                 160

Pro
```

(2) INFORMATION FOR SEQ ID NO:3:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..111

(xi) SEQUENCE DESCRIPTION: SEQ ID NO:3:

```
GAC AAT ACA CAT CCC TGC CAG TCT GAC ATG AAT ATC GAA GGA GCC TGG    48
Asp Asn Thr His Pro Cys Gln Ser Asp Met Asn Ile Glu Gly Ala Trp
 1               5                  10                  15

AAG AGA GGC TAC ACG GGA AAG AAC ATT GTG GTC ACT ATC CTG GAT GAC    96
Lys Arg Gly Tyr Thr Gly Lys Asn Ile Val Val Thr Ile Leu Asp Asp
            20                  25                  30

GGA ATT GAG AGA ACC                                                111
Gly Ile Glu Arg Thr
            35
```

(2) INFORMATION FOR SEQ ID NO:4:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Asn Thr His Pro Cys Gln Ser Asp Met Asn Ile Glu Gly Ala Trp
 1               5                  10                  15

Lys Arg Gly Tyr Thr Gly Lys Asn Ile Val Val Thr Ile Leu Asp Asp
            20                  25                  30

Gly Ile Glu Arg Thr
            35
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( i x ) FEATURE:
        ( A ) NAME/KEY: Xaa = Lys or Arg
        ( B ) LOCATION: 1
        ( A ) NAME/KEY: Xaa = any amino acid
        ( B ) LOCATION: 2
        ( A ) NAME/KEY: Xaa = Lys, Arg, Ala or Pro
        ( B ) LOCATION: 3
        ( A ) NAME/KEY: Xaa = Lys or Arg
        ( B ) LOCATION: 4

( x i ) SEQUENCE DESCRIPTION: SEQ ID NO:5:

Xaa Xaa Xaa Xaa
1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Arg Glu Lys Arg
1

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:7:

TCCCGTCGAC HYCCCABSWR TGRRYDGWCA TGAA    34

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:8:

TGTCGGATCC TGYGGNGTHG GHGTDGCHTA YAAYKCC    37

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear (ii) MOLECULE TYPE: DNA (primer)

(xi) SEQUENCE DESCRIPTION: SEQ ID NO:9:

TCCCGTCGAC SGGDGCWGMD GCHGAKGTSC CHGWRTG    37

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:10:

CCAAGYATGT GGTAYATGCA YTGYAGY    27

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:11:

GGCTGCTCAG CCTTGGAATG TACATGTTTT    30

(2) INFORMATION FOR SEQ ID NO:12:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..918

(xi) SEQUENCE DESCRIPTION: SEQ ID NO:12:

```
TAT ATG CAC TGT AGC GAC AAT ACA CAT CCC TGC CAG TCT GAC ATG AAT      48
Tyr Met His Cys Ser Asp Asn Thr His Pro Cys Gln Ser Asp Met Asn
 1               5                  10                  15

ATC GAA GGA GCC TGG AAG AGA GGC TAC ACG GGA AAG AAC ATT GTG GTC      96
Ile Glu Gly Ala Trp Lys Arg Gly Tyr Thr Gly Lys Asn Ile Val Val
             20                  25                  30

ACT ATC CTG GAT GAC GGA ATT GAG AGA ACC CAT CCA GAT CTG ATG CAA     144
Thr Ile Leu Asp Asp Gly Ile Glu Arg Thr His Pro Asp Leu Met Gln
         35                  40                  45

AAC TAC GAT GCT CTG GCA NGT TGC GAC GTG AAT GGG AAT GAC TTG GAC     192
Asn Tyr Asp Ala Leu Ala Xaa Cys Asp Val Asn Gly Asn Asp Leu Asp
     50                  55                  60

CCA ATG CCT CGT TAT GAT GCA AGC AAC GAG AAC AAG CAT GGG ACT CGC     240
Pro Met Pro Arg Tyr Asp Ala Ser Asn Glu Asn Lys His Gly Thr Arg
 65                  70                  75                  80

TGT GCT GGA GAA GTG GCA GCC GCT GCA AAC AAT TCG CAC TGC ACA GTC     288
Cys Ala Gly Glu Val Ala Ala Ala Ala Asn Asn Ser His Cys Thr Val
                 85                  90                  95

GGA ATT GCT TTC AAC GCC AAG ATC GGA GGA GTG CGA NTG CTG GAC GGA     336
Gly Ile Ala Phe Asn Ala Lys Ile Gly Gly Val Arg Xaa Leu Asp Gly
            100                 105                 110
```

```
GAT  GTC  ACG  GAC  ATG  GTT  GAA  GCA  AAA  TCA  GTT  AGC  TTC  AAC  CCC  CAG     384
Asp  Val  Thr  Asp  Met  Val  Glu  Ala  Lys  Ser  Val  Ser  Phe  Asn  Pro  Gln
          115                 120                 125

CAC  GTG  CAC  ATT  TAC  AGC  GCC  AGC  TGG  GGC  CCG  GNT  GAT  GAT  GGC  AAG     432
His  Val  His  Ile  Tyr  Ser  Ala  Ser  Trp  Gly  Pro  Xaa  Asp  Asp  Gly  Lys
          130                 135                 140

ACT  GTG  GAC  GGA  CCA  GCC  CCC  CTC  ACC  CGG  NAA  GCC  TTT  GAA  AAC  GGC     480
Thr  Val  Asp  Gly  Pro  Ala  Pro  Leu  Thr  Arg  Lys  Ala  Phe  Glu  Asn  Gly
145                      150                 155                      160

GTT  AGA  ATG  GGG  CGG  AGA  GGC  CTC  GGN  TCT  GTG  TTT  GTT  TGG  GCA  TCT     528
Val  Arg  Met  Gly  Arg  Arg  Gly  Leu  Gly  Ser  Val  Phe  Val  Trp  Ala  Ser
                    165                 170                 175

GGA  AAT  GGT  GGA  AGG  AGC  AAA  GAC  CAC  TGC  TCC  TGT  GAT  GGC  TAC  ACC     576
Gly  Asn  Gly  Gly  Arg  Ser  Lys  Asp  His  Cys  Ser  Cys  Asp  Gly  Tyr  Thr
               180                 185                      190

AAC  AGC  ATC  TAC  ACC  ATC  TCC  ATC  AGC  AGC  ACT  GCA  GAA  AGC  GGA  AAG     624
Asn  Ser  Ile  Tyr  Thr  Ile  Ser  Ile  Ser  Ser  Thr  Ala  Glu  Ser  Gly  Lys
          195                 200                      205

AAA  CCT  TGG  TAC  CTG  GAA  GAG  TGT  TCA  TCC  ACG  CTG  GCC  ACA  ACC  TAC     672
Lys  Pro  Trp  Tyr  Leu  Glu  Glu  Cys  Ser  Ser  Thr  Leu  Ala  Thr  Thr  Tyr
     210                      215                 220

AGC  AGC  GGG  GAG  TCC  TAC  GAT  AAG  AAA  ATC  ATC  ACT  ACA  GAT  CTG  AGG     720
Ser  Ser  Gly  Glu  Ser  Tyr  Asp  Lys  Lys  Ile  Ile  Thr  Thr  Asp  Leu  Arg
225                      230                 235                      240

CAG  CGT  TGC  ACG  GAC  AAC  CAC  ACT  GGG  ACG  TCA  GCC  TCA  GCC  CCC  ATG     768
Gln  Arg  Cys  Thr  Asp  Asn  His  Thr  Gly  Thr  Ser  Ala  Ser  Ala  Pro  Met
                    245                 250                 255

GCT  GCA  GGC  ATC  ATT  GCG  CTG  GCC  CTG  GAA  GCC  AAT  CCG  TTT  CTG  ACC     816
Ala  Ala  Gly  Ile  Ile  Ala  Leu  Ala  Leu  Glu  Ala  Asn  Pro  Phe  Leu  Thr
               260                      265                 270

TGG  AGA  GAC  GTA  CAG  CAT  GTT  ATT  GTC  AGG  ACT  TCC  CGT  GCG  GGA  CAT     864
Trp  Arg  Asp  Val  Gln  His  Val  Ile  Val  Arg  Thr  Ser  Arg  Ala  Gly  His
          275                 280                      285

TTG  AAC  GCT  AAT  GAC  TGG  AAA  ACC  AAT  GCT  GCT  GGT  TTT  AAG  GTG  AGC     912
Leu  Asn  Ala  Asn  Asp  Trp  Lys  Thr  Asn  Ala  Ala  Gly  Phe  Lys  Val  Ser
     290                 295                 300

CAT  CTT                                                                            918
His  Leu
305
```

( 2 ) INFORMATION FOR SEQ ID NO:13:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Tyr  Met  His  Cys  Ser  Asp  Asn  Thr  His  Pro  Cys  Gln  Ser  Asp  Met  Asn
1                   5                   10                       15

Ile  Glu  Gly  Ala  Trp  Lys  Arg  Gly  Tyr  Thr  Gly  Lys  Asn  Ile  Val  Val
               20                  25                       30

Thr  Ile  Leu  Asp  Asp  Gly  Ile  Glu  Arg  Thr  His  Pro  Asp  Leu  Met  Gln
          35                  40                  45

Asn  Tyr  Asp  Ala  Leu  Ala  Xaa  Cys  Asp  Val  Asn  Gly  Asn  Asp  Leu  Asp
     50                  55                  60

Pro  Met  Pro  Arg  Tyr  Asp  Ala  Ser  Asn  Glu  Asn  Lys  His  Gly  Thr  Arg
65                  70                  75                       80
```

-continued

| Cys | Ala | Gly | Glu | Val | Ala | Ala | Ala | Asn | Asn | Ser | His | Cys | Thr | Val |
|-----|-----|-----|-----|-----|-----|-----|-----|-----|-----|-----|-----|-----|-----|-----|
|     |     |     |     | 85  |     |     |     |     | 90  |     |     |     |     | 95  |

Gly Ile Ala Phe Asn Ala Lys Ile Gly Gly Val Arg Xaa Leu Asp Gly
            100             105                 110

Asp Val Thr Asp Met Val Glu Ala Lys Ser Val Ser Phe Asn Pro Gln
        115             120                 125

His Val His Ile Tyr Ser Ala Ser Trp Gly Pro Xaa Asp Asp Gly Lys
    130                 135                 140

Thr Val Asp Gly Pro Ala Pro Leu Thr Arg Xaa Ala Phe Glu Asn Gly
145                 150                 155                 160

Val Arg Met Gly Arg Arg Gly Leu Gly Ser Val Phe Val Trp Ala Ser
            165                 170                 175

Gly Asn Gly Gly Arg Ser Lys Asp His Cys Ser Cys Asp Gly Tyr Thr
            180                 185                 190

Asn Ser Ile Tyr Thr Ile Ser Ile Ser Ser Thr Ala Glu Ser Gly Lys
        195                 200                 205

Lys Pro Trp Tyr Leu Glu Glu Cys Ser Ser Thr Leu Ala Thr Thr Tyr
    210                 215                 220

Ser Ser Gly Glu Ser Tyr Asp Lys Lys Ile Ile Thr Thr Asp Leu Arg
225                 230                 235                 240

Gln Arg Cys Thr Asp Asn His Thr Gly Thr Ser Ala Ser Ala Pro Met
            245                 250                 255

Ala Ala Gly Ile Ile Ala Leu Ala Leu Glu Ala Asn Pro Phe Leu Thr
            260                 265                 270

Trp Arg Asp Val Gln His Val Ile Val Arg Thr Ser Arg Ala Gly His
        275                 280                 285

Leu Asn Ala Asn Asp Trp Lys Thr Asn Ala Ala Gly Phe Lys Val Ser
    290                 295                 300

His Leu
305

( 2 ) INFORMATION FOR SEQ ID NO:14:

( i ) SEQUENCE CHARACTERISTICS:
           ( A ) LENGTH: 867 base pairs
           ( B ) TYPE: nucleic acid
           ( C ) STRANDEDNESS: single
           ( D ) TOPOLOGY: linear ( i i ) MOLECULE TYPE: cDNA ( i x ) FEATURE:
           ( A ) NAME/KEY: CDS
           ( B ) LOCATION: 1..867

( x i ) SEQUENCE DESCRIPTION: SEQ ID NO:14:

```
GAC TAT GGC ACA GAG GAT TAT GCA GGT CCC TGC GAC CCT GAG TGC AGT      48
Asp Tyr Gly Thr Glu Asp Tyr Ala Gly Pro Cys Asp Pro Glu Cys Ser
 1               5                  10                  15

GAG GTT GGC TGT GAC GGG CCA GGA CCA GAC CAC TGC AAT GAC TGT TTG      96
Glu Val Gly Cys Asp Gly Pro Gly Pro Asp His Cys Asn Asp Cys Leu
            20                  25                  30

CAC TAC TAC TAC AAG CTG AAA AAC AAT ACC AGG ATC TGT GTC TCC AGC     144
His Tyr Tyr Tyr Lys Leu Lys Asn Asn Thr Arg Ile Cys Val Ser Ser
        35                  40                  45

TGC CCC CCT GGC CAC TAC CAC GCC GAC AAG AAG CGC TGC AGG AAG TGT     192
Cys Pro Pro Gly His Tyr His Ala Asp Lys Lys Arg Cys Arg Lys Cys
    50                  55                  60

GCC CCC AAC TGT GAG TCC TGC TTT GGG AGC CAT GGT GAC CAA TGC ATG     240
Ala Pro Asn Cys Glu Ser Cys Phe Gly Ser His Gly Asp Gln Cys Met
```

```
                65                         70                         75                         80
TCC  TGC  AAA  TAT  GGA  TAC  TTT  CTG  AAT  GAA  GAA  ACC  AAC  AGC  TGT  GTT                288
Ser  Cys  Lys  Tyr  Gly  Tyr  Phe  Leu  Asn  Glu  Glu  Thr  Asn  Ser  Cys  Val
               85                         90                         95

ACT  CAC  TGC  CCT  GAT  GGG  TCA  TAT  CAG  GAT  ACC  AAG  AAA  AAT  CTT  TGC                336
Thr  His  Cys  Pro  Asp  Gly  Ser  Tyr  Gln  Asp  Thr  Lys  Lys  Asn  Leu  Cys
               100                        105                        110

CGG  AAA  TGC  AGT  GAA  AAC  TNC  AAG  ACA  TGT  ACT  GAA  TTC  CAT  ANC  TGT                384
Arg  Lys  Cys  Ser  Glu  Asn  Xaa  Lys  Thr  Cys  Thr  Glu  Phe  His  Xaa  Cys
               115                        120                        125

ACA  GAA  TGT  AGG  GAT  GGG  TTA  AGC  CTN  CAG  GGA  TCC  CGG  TGC  TCT  GTC                432
Thr  Glu  Cys  Arg  Asp  Gly  Leu  Ser  Leu  Gln  Gly  Ser  Arg  Cys  Ser  Val
     130                        135                        140

TCC  TGT  GAA  GAT  GGA  CGG  TAT  TTC  ANC  GGC  CAG  GAC  TGC  CAG  CCC  TGC                480
Ser  Cys  Glu  Asp  Gly  Arg  Tyr  Phe  Xaa  Gly  Gln  Asp  Cys  Gln  Pro  Cys
145                        150                        155                        160

CAC  CGC  TNC  TNC  GCC  ACT  TGT  GCT  GGG  GCA  GGA  GCT  GAT  GGG  TGC  ATT                528
His  Arg  Xaa  Xaa  Ala  Thr  Cys  Ala  Gly  Ala  Gly  Ala  Asp  Gly  Cys  Ile
                    165                        170                        175

AAC  TGC  ACA  GAG  GGC  TAC  TTC  ATG  GAG  GAT  GGG  AGA  TGC  GTG  CAG  ANC                576
Asn  Cys  Thr  Glu  Gly  Tyr  Phe  Met  Glu  Asp  Gly  Arg  Cys  Val  Gln  Xaa
               180                        185                        190

TGT  AGT  ATC  AGC  TAT  TAC  TTT  GAC  CAC  TCT  TCA  GAG  AAT  GGA  TAC  AAA                624
Cys  Ser  Ile  Ser  Tyr  Tyr  Phe  Asp  His  Ser  Ser  Glu  Asn  Gly  Tyr  Lys
               195                        200                        205

TCC  TGC  AAA  AAA  TGT  GAT  ATC  AGT  TGT  TTG  ACG  TGC  AAT  GGC  CCA  GGA                672
Ser  Cys  Lys  Lys  Cys  Asp  Ile  Ser  Cys  Leu  Thr  Cys  Asn  Gly  Pro  Gly
     210                        215                        220

TTC  AAG  AAC  TGT  ACA  AGC  TGC  CCT  AGT  GGG  TAT  CTC  TTA  GAC  TTA  GGA                720
Phe  Lys  Asn  Cys  Thr  Ser  Cys  Pro  Ser  Gly  Tyr  Leu  Leu  Asp  Leu  Gly
225                        230                        235                        240

ATG  TGT  CAA  ATG  GGA  GCC  ATT  TGC  AAG  GAT  GCA  ACG  GAA  GAG  TCC  TGG                768
Met  Cys  Gln  Met  Gly  Ala  Ile  Cys  Lys  Asp  Ala  Thr  Glu  Glu  Ser  Trp
               245                        250                        255

GCG  GAA  GGA  GGC  TTC  TGT  ATG  CTT  GTG  AAA  AAG  AAC  AAT  CTG  TGC  CAA                816
Ala  Glu  Gly  Gly  Phe  Cys  Met  Leu  Val  Lys  Lys  Asn  Asn  Leu  Cys  Gln
               260                        265                        270

CGG  AAG  GTT  CTT  CAA  CAA  CTT  TGC  TGC  AAA  ACA  TGT  ACA  TTC  CAA  GGC                864
Arg  Lys  Val  Leu  Gln  Gln  Leu  Cys  Cys  Lys  Thr  Cys  Thr  Phe  Gln  Gly
          275                        280                        285

TGA                                                                                            867
```

( 2 ) INFORMATION FOR SEQ ID NO:15:

( i ) SEQUENCE CHARACTERISTICS:
        ( A ) LENGTH: 288 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Asp  Tyr  Gly  Thr  Glu  Asp  Tyr  Ala  Gly  Pro  Cys  Asp  Pro  Glu  Cys  Ser
 1              5                        10                        15

Glu  Val  Gly  Cys  Asp  Gly  Pro  Gly  Asp  His  Cys  Asn  Asp  Cys  Leu
               20                        25                        30

His  Tyr  Tyr  Tyr  Lys  Leu  Lys  Asn  Asn  Thr  Arg  Ile  Cys  Val  Ser  Ser
               35                        40                        45

Cys  Pro  Pro  Gly  His  Tyr  His  Ala  Asp  Lys  Lys  Arg  Cys  Arg  Lys  Cys
     50                        55                        60
```

-continued

| | | | | | | | | | | | | | | | |
|---|---|---|---|---|---|---|---|---|---|---|---|---|---|---|---|
| Ala | Pro | Asn | Cys | Glu | Ser | Cys | Phe | Gly | Ser | His | Gly | Asp | Gln | Cys | Met |
| 65 | | | | | 70 | | | | | 75 | | | | | 80 |
| Ser | Cys | Lys | Tyr | Gly | Tyr | Phe | Leu | Asn | Glu | Glu | Thr | Asn | Ser | Cys | Val |
| | | | | 85 | | | | | 90 | | | | | 95 | |
| Thr | His | Cys | Pro | Asp | Gly | Ser | Tyr | Gln | Asp | Thr | Lys | Lys | Asn | Leu | Cys |
| | | | 100 | | | | | 105 | | | | | 110 | | |
| Arg | Lys | Cys | Ser | Glu | Asn | Xaa | Lys | Thr | Cys | Thr | Glu | Phe | His | Xaa | Cys |
| | | 115 | | | | | 120 | | | | | 125 | | | |
| Thr | Glu | Cys | Arg | Asp | Gly | Leu | Ser | Leu | Gln | Gly | Ser | Arg | Cys | Ser | Val |
| | 130 | | | | | 135 | | | | | 140 | | | | |
| Ser | Cys | Glu | Asp | Gly | Arg | Tyr | Phe | Xaa | Gly | Gln | Asp | Cys | Gln | Pro | Cys |
| 145 | | | | | 150 | | | | | 155 | | | | | 160 |
| His | Arg | Xaa | Xaa | Ala | Thr | Cys | Ala | Gly | Ala | Gly | Ala | Asp | Gly | Cys | Ile |
| | | | | 165 | | | | | 170 | | | | | 175 | |
| Asn | Cys | Thr | Glu | Gly | Tyr | Phe | Met | Glu | Asp | Gly | Arg | Cys | Val | Gln | Xaa |
| | | | 180 | | | | | 185 | | | | | 190 | | |
| Cys | Ser | Ile | Ser | Tyr | Tyr | Phe | Asp | His | Ser | Ser | Glu | Asn | Gly | Tyr | Lys |
| | | 195 | | | | | 200 | | | | | 205 | | | |
| Ser | Cys | Lys | Lys | Cys | Asp | Ile | Ser | Cys | Leu | Thr | Cys | Asn | Gly | Pro | Gly |
| | 210 | | | | | 215 | | | | | 220 | | | | |
| Phe | Lys | Asn | Cys | Thr | Ser | Cys | Pro | Ser | Gly | Tyr | Leu | Leu | Asp | Leu | Gly |
| 225 | | | | | 230 | | | | | 235 | | | | | 240 |
| Met | Cys | Gln | Met | Gly | Ala | Ile | Cys | Lys | Asp | Ala | Thr | Glu | Glu | Ser | Trp |
| | | | | 245 | | | | | 250 | | | | | 255 | |
| Ala | Glu | Gly | Gly | Phe | Cys | Met | Leu | Val | Lys | Lys | Asn | Asn | Leu | Cys | Gln |
| | | | 260 | | | | | 265 | | | | | 270 | | |
| Arg | Lys | Val | Leu | Gln | Gln | Leu | Cys | Cys | Lys | Thr | Cys | Thr | Phe | Gln | Gly |
| | | 275 | | | | | 280 | | | | | 285 | | | |

CD4+ T-LYMPHOCTYE PROTEASES AND GENES ENCODING SAID PROTEASES

CROSS-REFERENCE TO RELATED APPLICATIONS

The present application is a continuation-in-part of U.S. patent application Ser. No. 08/088,322, entitled "Yeast Assay to Identify Inhibitors of Dibasic Amino Acid Processing Endoproteases", filed Jul. 7, 1993 now U.S. Pat. No. 5,413,914, which is incorporated by reference herein in its entirety. The present application is also a continuation-in-part of pending U.S. patent application Ser. No. 08/340,185, entitled "Yeast-Based Delivery Vehicles", filed Nov. 15, 1994, which is incorporated by reference herein in its entirety. Ser. No. 08/340,185 is a continuation-in-part of Ser. No. 08/088,322.

This invention was made at least in part with government support under Grant No. AI 34747, awarded by the National Institute of Allergy and Infectious Diseases, National Institutes of Health. The government has certain rights to this invention.

FIELD OF THE INVENTION

The present invention is directed to novel dibasic amino acid processing endoprotease genes and to novel proteins encoded by such genes. More particularly, the present invention is directed to a novel human CD4+ T-lymphocyte dibasic amino acid processing endoprotease gene and the protein encoded by that gene. The present invention also includes use of such genes and proteins to develop therapeutic compositions that enhance or inhibit dibasic amino acid processing endoprotease activity.

BACKGROUND OF THE INVENTION

A number of enveloped viruses, including retroviruses, hepatitis viruses, herpes viruses, orthomyxoviruses and paramyxoviruses, produce precursor envelope glycoproteins that require cleavage by a cellular dibasic amino acid processing endoprotease as one step in the process of envelope glycoprotein maturation. As precursor envelope glycoproteins are being synthesized, they are directed into the host cell secretory pathway for transport to the cell surface. As the precursor proteins move through the pathway, they are subjected to a variety of post-translational events including glycosylation and proteolytic cleavage (see, for example, Stein et al., 1990, *J. Biol. Chem.* 265, 2640–2649). The precursor human immunodeficiency virus (HIV) envelope protein gp160, for example, is co-translationally glycosylated and subsequently cleaved into gp120 and gp41 by a cellular dibasic amino acid processing endoprotease that apparently is localized in the Golgi apparatus. The gp120 and gp41 proteins are further glycosylated prior to reaching the infected cell surface. Cleavage of the HIV gp160 protein has been shown to be necessary for membrane fusion, syncytium formation and viral infectivity (see, for example, McCune et al., 1988, *Cell* 53, 55–67; Kowalski et al., 1987, *Science* 237, 1351–1355).

Although the genes encoding several dibasic amino acid processing endoproteases (also referred to as subtilisin-like protein convertases) have been isolated (see, for example, Barr, 1991, *Cell* 66, 1–3; Hakes et al., 1991, *Endocrinology* 129, 3053–3063; Kiefer et al., 1991, *DNA and Cell Biology* 10, 757–769; Lusson et al., 1993, *Proc. Natl. Acad. Sci. USA* 90, 6691–6695; Steiner et al., 1992, *J. Biol. Chem.* 267, 23435–23438, a number of cellular dibasic amino acid processing endoproteases remain to be identified, including CD4+ T-lymphocyte dibasic amino acid processing endoproteases responsible for cleaving the precursor envelope proteins of lentiviruses and lymphotropic viruses into envelope proteins, such as the enzyme that cleaves HIV gp160 into gp120 and gp41 in vivo. There is a need to identify cellular dibasic amino acid processing endoproteases that are responsible for in vivo cleavage of targeted substrates. Investigators have shown, for example, that the extent of proteolytic cleavage is a function of the sequence of amino acids at the dibasic amino acid processing site and of the dibasic amino acid processing endoprotease for hormones such as insulin and renin (see, for example, Oda et al., 1991, *Biochem. Biophys. Res. Comm.* 179, 1181–1186; Thim et al., 1986, *Proc. Natl. Acad. Sci. USA* 83, 6766–6770.

Nucleoside analogs are currently in use as antiviral drugs, particularly for treating retroviral infections as the analogs can inhibit the ability of the retroviral reverse transcriptase enzyme to make a DNA copy of the incoming viral RNA. For example, HIV infections are being treated with AZT (3'-azidothymidine), ddI (2'3'-dideoxyinosine), ddC (2'3'-dideoxycytidine), and d4T (didehydrothymidine). Nucleoside analogs, however, have short half-lives and can exhibit substantial side effects. In addition, viruses often develop resistance to the nucleoside analog within a short period time of its administration.

Non-nucleoside inhibitors of HIV reverse transcriptase, such as TIBO (tetrahydro-imidazo(4,5,1-jk)(1,4)-benzodiazepin-2(1H)-one), BI-RG-587 (11-cyclopropyl-7-methyldipyrido-(2,3-b:3'3'-f)1,4-diazepin-6H-5-one), pyridones, and bis(heteroaryl)piperazines, are also being developed and tested. Since these compounds are highly selective for the HIV reverse transcriptase enzyme, they apparently cause less severe side effects than do nucleoside analogs. Decreased sensitivity of HIV to these agents, however, also develops rapidly.

The HIV-encoded aspartyl protease that processes the gag and gag/pol polyproteins to yield the mature structural proteins and enzymes required for virion formation (p24, p17, p15, reverse transcriptase) has also been targeted as an enzyme against which to design antiviral agents. HIV protease inhibitors, at least theoretically, can inhibit HIV production by chronically infected cells and, as such, have an advantage over reverse transcriptase inhibitors that apparently can only block replication if added to cells before HIV infection. Peptide-based substrate analogs are being prepared and tested. One persistent drawback of HIV protease inhibitors is the emergence of HIV strains that are resistant to the inhibitor being administered.

Other strategies for inhibiting HIV infection that are being pursued include inhibition of other HIV-encoded proteins such as Tat, Rev, and integrase; blocking entry of the virus into the cell by, for example, soluble CD4 receptor molecules; targeted delivery of toxins to HIV-infected cells; inhibition of viral functions using antisense technology; and immune constitution protocols. Although several of these technologies are at the early stages of development, clinical trials conducted using some of these technologies have been disappointing. For a recent review of present and future strategies to treat HIV infection, see Johnston et al., 1993, *Science* 260, 1286–1293.

Most assays used to test antiviral drugs are either in vitro or mammalian cell culture assays, many relying on the use of infectious virus. Mammalian cell culture assays are usually costly, complex, time-consuming, and potentially dangerous if infectious virus is used. Recently, a Drosophila cell-based assay was developed for screening inhibitors of the HIV Rev protein. For a review of methods to identify HIV inhibitors, see Johnston et al., ibid.

Thus, there remains a need to identify antiviral drugs with improved efficacy that have fewer side effects than known drugs and against which an infected host is less likely to develop resistance. A preferred class of inhibitors to identify are those that can be used to treat infectious diseases, such as HIV infections, in which proliferation of the infectious agent depends on dibasic amino acid processing endoprotease cleavage. In order to identify such drugs in a rapid and straightforward manner, an improved assay is required that is less complex, less expensive, less time-consuming, and more selective than currently used methods. There is also a need to identify CD4+ T-lymphocyte dibasic amino acid processing endoproteases, such as the enzyme that cleaves HIV gp160 in vivo, in order to identify specific inhibitors having greater selectivity and, hence, fewer side effects.

SUMMARY OF THE INVENTION

The present invention includes the identification and isolation of a gene encoding a dibasic amino acid processing endoprotease from CD4+ T-lymphocytes as well as a protein encoded by that gene. The present invention also includes use of such genes and proteins in a number of applications, including use of proteins of the present invention to identify compounds that are particularly useful therapeutic compositions in that they can treat infectious diseases susceptible to inhibition of dibasic amino acid processing endoprotease activity with improved efficacy and with fewer side effects than compounds that are currently employed.

One embodiment of the present invention is an isolated nucleic acid molecule that includes the dibasic amino acid processing endoprotease gene nhTCP and nucleic acid molecules that include fragments of such a gene that encode a dibasic amino acid processing endoprotease having proteolytic activity. Another embodiment of the present invention is an isolated nucleic acid molecule that includes a nucleic acid sequence having at least about 86 percent nucleic acid sequence identity with SEQ ID NO:1, a nucleic acid sequence having at least about 93 percent nucleic acid sequence identity with SEQ ID NO:3, a nucleic acid molecule comprising a nucleic acid sequence having at least about 86 percent nucleic acid sequence identity with SEQ ID NO:12 and/or a nucleic acid molecule comprising a nucleic acid sequence having at least about 86 percent nucleic acid sequence identity with SEQ ID NO:14. Yet another embodiment of the present invention is an isolated nucleic acid molecule that is capable of hybridizing under stringent conditions with a regulatory region of a dibasic amino acid processing endoprotease gene comprising nhTCP. Particularly preferred nucleic acid molecules include nhTCP$_{483}$, nhTCP$_{-2400}$ and/or nhTCP.

The present invention also includes recombinant molecules that include nucleic acid molecules of the present invention operatively linked to a transcription control sequence as well as recombinant cells that include nucleic acid molecules of the present invention.

One embodiment of the present invention is a recombinant cell comprising a cell transformed with a nucleic acid molecule capable of hybridizing, under stringent conditions, with a dibasic amino acid processing endoprotease gene comprising nhTCP, wherein the cell is capable of expressing the nucleic acid molecule.

Also included in the present invention are isolated proteins encoded by nucleic acid molecules of the present invention as well as isolated antibodies capable of selectively binding to such proteins. As such, proteins of the present invention can be encoded by (a) a nucleic acid molecule that includes a dibasic amino acid processing endoprotease gene nhTCP, (b) a nucleic acid molecule that includes a fragment of such a gene such that the fragment encodes a dibasic amino acid processing endoprotease having proteolytic activity, (c) a nucleic acid molecule that includes a nucleic acid sequence having at least about 86 percent nucleic acid sequence identity with SEQ ID NO:1, (d) a nucleic acid molecule that includes a nucleic acid sequence having at least about 93 percent nucleic acid sequence identity with SEQ ID NO:3, (e) a nucleic acid molecule that includes a nucleic acid sequence having at least about 86 percent nucleic acid sequence identity with SEQ ID NO:12 and/or (f) a nucleic acid molecule that includes a nucleic acid sequence having at least about 86 percent nucleic acid sequence identity with SEQ ID NO:14.

The present invention also includes a therapeutic composition capable of reducing the infectivity of an infectious agent susceptible to inhibition of dibasic amino acid processing endoprotease activity. Such a composition can include a nucleic acid molecule capable of hybridizing under stringent conditions with a dibasic amino acid processing endoprotease gene comprising nhTCP and/or a compound that inhibits dibasic amino acid processing endoprotease activity, wherein the compound is identified by its ability to inhibit the activity of hTCP. A therapeutic composition of the present invention also includes an excipient.

Another embodiment of the present invention is a method to protect an animal from disease caused by an infectious agent susceptible to inhibition of dibasic amino acid processing endoprotease activity. The method includes the step of administering to the animal a therapeutic composition that includes a nucleic acid molecule capable of hybridizing under stringent conditions with a dibasic amino acid processing endoprotease gene that includes nhTCP and/or a compound that inhibits dibasic amino acid processing endoprotease activity, wherein the compound is identified by its ability to inhibit the activity of hTCP.

Yet another embodiment of the present invention is a method to identify a compound that inhibits proteolytic cleavage by a dibasic amino acid processing endoprotease encoded by a nucleic acid molecule that is capable of hybridizing under stringent conditions with a dibasic amino acid processing endoprotease gene comprising nhTCP. The method includes the steps of (a) contacting a Kex2 endoprotease-deficient yeast strain transformed with the nucleic acid molecule and containing a precursor protein having a dibasic amino acid processing site with a putative inhibitory compound under conditions in which, in the absence of the compound, the yeast strain is capable of effecting cleavage of the precursor protein into cleavage products; and (b) assaying for production of at least one of the cleavage products. Production of a reduced amount of at least one of the cleavage products in the presence of the putative inhibitory compound compared to in the absence of the putative inhibitory compound indicates that the compound is able to inhibit proteolytic cleavage by the endoprotease. Also included in the present invention is a Kex2 endoprotease-deficient yeast strain transformed with a nucleic acid molecule that is capable of hybridizing under stringent conditions with a dibasic amino acid processing endoprotease gene that includes nhTCP. Also included in the present invention are inhibitors identified using such a method.

The present invention also includes a test kit to identify a compound capable of inhibiting a dibasic amino acid processing endoprotease encoded by a nucleic acid molecule that is capable of hybridizing under stringent conditions with a dibasic amino acid processing endoprotease gene that includes nhTCP. Such a test kit includes (a) a Kex2 endoprotease-deficient yeast strain transformed with the nucleic acid molecule and containing a precursor protein having a dibasic amino acid processing site, the yeast strain being capable of effecting cleavage of the precursor protein into cleavage products, and (b) a means for determining the extent of cleavage by the yeast strain in the presence of a putative inhibitory compound. The determining means includes a means for assaying for production of the cleavage products. Production of a reduced amount of cleavage products in the presence of the putative inhibitory compound compared to in the absence of the putative inhibitory compound indicates that the compound is able to inhibit proteolytic cleavage by the endoprotease. Also included in the present invention are inhibitors identified using such a test kit.

Another embodiment of the present invention is a method to identify a compound capable of inhibiting a dibasic amino acid processing endoprotease. Such a method includes the steps of (a) contacting a putative inhibitory compound with a secreted soluble dibasic amino acid processing endoprotease protein, wherein the endoprotease protein is encoded by a nucleic acid molecule that is capable of hybridizing under stringent conditions with a dibasic amino acid processing endoprotease gene comprising nhTCP and wherein the endoprotease protein is contacted in the presence of a precursor protein having a dibasic amino acid processing site under conditions in which, in the absence of the compound, the endoprotease protein is capable of effecting cleavage of the precursor protein into cleavage products; and (b) assaying for production of the cleavage products. Production of a reduced amount of cleavage products in the presence of the putative inhibitory compound compared to in the absence of the putative inhibitory compound indicates that the compound is able to inhibit proteolytic cleavage by the endoprotease. Also included in the present invention are inhibitors identified using such a method.

DETAILED DESCRIPTION OF THE INVENTION

The present invention includes the identification and isolation of a gene encoding a dibasic amino acid processing endoprotease from CD4+ T-lymphocytes as well as a protein encoded by that gene. Without being bound by theory, such a protein is believed to be the enzyme naturally responsible for the cleavage of precursor proteins having dibasic amino acid processing sites that are produced by CD4+ T-lymphocytes. Such precursor proteins include, but are not limited to, precursors of growth factors and other hormones as well as precursor proteins of infectious agents, such as immunodeficiency viruses that infect CD4+ T-lymphocytes. Genes and proteins of the present invention can be used in a number of applications, including those discussed below. Examples include the development of therapeutic compositions to reduce the infectivity of infectious agents having dibasic amino acid processing sites, to reduce excessive production of proteins that as precursors have dibasic amino acid processing sites and to enhance production of desired proteins, the precursors of which have dibasic amino acid processing sites.

The present invention also includes the surprising discovery that the dibasic amino acid processing endoprotease gene isolated from human CD4+ T-lymphocytes, as well as the protein encoded by that gene, is remarkably similar, at least in the catalytic domain, to mouse and rat PC5 genes and proteins (for sequences of rat and mouse PC5 genes and proteins, see Lusson et al. ibid.). (As used herein, a catalytic domain can be as small as the minimal amount of nucleic acid sequence that is required to encode a dibasic amino acid processing endoprotease protein having proteolytic activity. As can be appreciated by those skilled in the art, such a domain can consist of contiguous or noncontiguous nucleic acid sequences.) The present invention also includes the use of such nucleic acid molecules and proteins encoded therefrom, as well as other nucleic acid molecules that form stringent hybrids with the human gene of the present invention and proteins encoded therefrom, as therapeutic compositions and as tools to identify compounds that inhibit infection by infectious agents that are susceptible to inhibition of dibasic amino acid processing endoprotease activity. The inventors are not aware of any suggested or actual use of such molecules in such an embodiment.

The term dibasic amino acid processing endoprotease refers to any proteolytic enzyme that cleaves a precursor protein (also referred to as a proprotein) at a dibasic amino acid processing site within the precursor protein. Dibasic amino acid processing endoproteases are typically serine proteases of the subtilisin family, such as those described by Steiner et al., ibid.

The phrase dibasic amino acid processing site refers to a site on the precursor protein that can be cleaved by a dibasic amino acid processing endoprotease. Dibasic amino acid processing sites usually include at least one pair of basic amino acid residues that are substantially adjacent to each other. Suitable sites include, but are not limited to, Lys-Arg, Arg-Arg, Lys-Lys, Pro-Arg, Ala-Arg, Lys/Arg-X-Lys/Arg, and Lys/Arg-X-$X_1$-Lys/Arg (also referred to herein as SEQ ID NO:5), where "Lys" is lysine, "Arg" is arginine, "Pro" is proline, "Ala" is alanine, "X" is any amino acid, and "$X_1$" is preferably Lys, Arg, Ala or Pro. A particularly preferred dibasic amino acid processing site to target, particularly with inhibitory compounds of the present invention, is the Arg-Glu-Lys-Arg (also referred to herein as SEQ ID NO:6) site found in HIV gp160 precursor proteins, wherein "Glu" is glutamic acid.

The term precursor protein refers to a protein that undergoes post-translational modification during maturation, a process that includes at least one step of cleavage by a dibasic amino acid processing endoprotease at a dibasic amino acid processing site within the precursor protein to form at least one cleavage protein. The terms cleavage protein, cleaved protein, cleavage product, and cleaved product each refer to a protein that has been produced by proteolytic cleavage of a precursor protein, the cleavage being required, but not necessarily sufficient, for the protein to become mature and bioactive. It should be understood that cleavage proteins of the present invention can undergo additional post-translational maturation steps prior and/or subsequent to dibasic amino acid processing endoprotease cleavage. A precursor protein of the present invention can be a polyprotein such that the precursor protein contains more than one product which can be separated by cleavage with a dibasic amino acid processing endoprotease.

The present invention includes a number of novel nucleic acid molecules as well as the use of those and additional similar nucleic acid molecules in a variety of embodiments as disclosed herein. One embodiment of the present invention is an isolated nucleic acid molecule that includes the dibasic amino acid processing endoprotease gene nhTCP (defined below) and nucleic acid molecules that include fragments of that gene that encode a dibasic amino acid processing endoprotease having proteolytic activity. As used herein, the gene nhTCP includes all natural allelic variants of that gene. Methods to produce fragments and to identify those that encode proteins having proteolytic activity are known to those skilled in the art; examples are provided herein.

An isolated nucleic acid molecule of the present invention can include at least one of the following isolated nucleic acid molecules: a nucleic acid molecule that includes a nucleic acid sequence having at least about 86 percent nucleic acid sequence identity with SEQ ID NO:1, a nucleic acid molecule that includes a nucleic acid sequence having at least about 93 percent nucleic acid sequence identity with SEQ ID NO:3, a nucleic acid molecule that includes a nucleic acid sequence having at least about 86 percent nucleic acid sequence identity with SEQ ID NO:12 and a nucleic acid molecule that includes a nucleic acid sequence having at least about 86 percent nucleic acid sequence identity with SEQ ID NO:14. As will be disclosed in further detail below, SEQ ID NO:1, SEQ ID NO:3 and SEQ ID NO:12 are each believed to include sequences encoding at least part of the catalytic domain (i.e., active site) of a dibasic amino acid processing endoprotease.

Isolated nucleic acid molecules of the present invention can also be nucleic acid molecules that include regions capable of hybridizing under stringent conditions with a regulatory region of the dibasic amino acid processing endoprotease gene nhTCP (i.e., with a region that controls expression of the gene hTCP).

A preferred isolated nucleic acid molecule of the present invention has at least about 75 percent, preferably at least about 80 percent, more preferably at least about 85 percent, and even more preferably at least about 90 percent nucleic acid sequence identity with nhTCP. As used herein, percent nucleic acid sequence identity refers to the percentage of identical sequences within corresponding regions of two nucleic acid molecules. Such regions can be of a size spanning from the minimal length required for two molecules to form a stringent hybrid to the entire gene.

The present invention also includes the use of any isolated nucleic acid molecule capable of hybridizing, under stringent conditions, with (i.e., to) a human CD4+ T-lymphocyte dibasic amino acid processing endoprotease gene referred to herein as nhTCP, or human T cell protease gene. As such, all of these nucleic acid molecules are also included in the present invention.

As used herein, the gene nhTCP includes all nucleic acid sequences related to a natural nhTCP gene, such as regulatory regions that control production of a human T cell dibasic amino acid processing endoprotease encoded by that gene (e.g., transcription, translation or post-translation control regions) as well as the coding region itself. The gene nhTCP of the present invention can be distinguished from other dibasic amino acid processing endoprotease genes in that nhTCP includes nhTCP$_{483}$, a cDNA (complementary DNA) nucleic acid molecule, the production of which is disclosed in the Examples, and the deduced nucleic acid sequence of the coding strand of which is presented herein as SEQ ID NO:1. The protein encoded by nhTCP$_{483}$, referred to herein as hTCP$_{161}$, has a deduced amino acid sequence presented herein as SEQ ID NO:2. (It should be noted that since nucleic acid and amino acid sequencing technologies are not entirely error-free, SEQ ID NO:1, as well as other SEQ ID NOs disclosed herein, represent, at best, apparent sequences of the respective nucleic acid molecules and proteins.) As used herein, stringent hybridization conditions refer to standard hybridization conditions under which nucleic acid molecules, including oligonucleotides, are used to identify similar sequences. Such standard conditions are disclosed, for example, in Sambrook et al., *Molecular Cloning: A Laboratory Manual*, Cold Spring Harbor Labs Press, 1989. Examples of such conditions are provided in the Examples section. It should be noted that the extent of identity required to form a stable hybrid can vary depending on whether the sequences shared between two molecules are interspersed throughout the nucleic acid molecules or are clustered (i.e., localized) in distinct regions on the nucleic acid molecules.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with that nucleic acid sequence under stringent hybridization conditions. Nucleic acid molecules of the present invention, therefore, can be derived from any source having a nucleic acid molecule that hybridizes under stringent hybridization conditions with nhTCP. Preferred sources include animals, with mammals, birds, amphibians, insects and fish being more preferred, and with humans, other primates, cats, dogs, cattle, horses, swine, sheep and rodents as well as other pets and livestock being even more preferred. An isolated nucleic acid molecule of the present invention can also be produced using recombinant DNA technology (e.g., polymerase chain reaction (PCR) amplification, cloning) or chemical synthesis.

Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein of the present invention and/or to form stable hybrids under stringent conditions with natural isolates. As such, a nucleic acid molecule of the present invention can include any natural gene or a homologue thereof capable of hybridizing to nhTCP. It is to be noted that, as used herein, homologues of a nucleic acid molecule include portions of that nucleic acid molecule. A nucleic acid molecule of the present invention can include one or more regulatory regions, full-length or partial coding regions, or combinations thereof. The minimal size of a nucleic acid molecule of the present invention is the minimal size capable of forming a stable hybrid under stringent hybridization conditions with nhTCP.

A nucleic acid molecule homologue of the present invention can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., dibasic amino acid processing endoprotease activity, ability to induce production of a desirable antibody) and/or by hybridization with nhTCP under stringent conditions.

A nucleic acid molecule of the present invention can include a nucleic acid sequence that encodes a dibasic amino acid processing endoprotease protein, which preferably has proteolytic activity (i.e., can cleave a protein at a dibasic amino acid processing site). It is to be noted that the term "a" or "an" entity refers to one or more of that entity; as such, the terms "a" (or "an"), "one or more" and "at least one" can be used interchangeably herein. It is also to be noted that although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Dibasic amino acid processing endoprotease proteins of the present invention include, but are not limited to, full-length proteins, proteins that are truncates thereof and fusion proteins. Examples of such proteins are disclosed below. A particularly preferred nucleic acid molecule of the present invention includes a nucleic acid sequence that encodes a human CD4+ T-lymphocyte dibasic amino acid processing endoprotease protein, which preferably has proteolytic activity.

Various embodiments of the present invention involve use of an isolated nucleic acid molecule that is capable of hybridizing, under stringent conditions, with a nucleic acid molecule comprising $nhTCP_{483}$. As used herein, a nucleic acid molecule that comprises $nhTCP_{483}$ refers to a nucleic acid molecule that includes $nhTCP_{483}$; such a nucleic acid molecule therefore can include nucleic acid sequences in addition to $nhTCP_{483}$ or can consist only of $nhTCP_{483}$. As such, nucleic acid molecules of this embodiment can include nhTCP, or any portion thereof (i.e., any region that is capable of hybridizing to a region of nhTCP). Additional nucleic acid molecules of this embodiment include nucleic acid molecules that are sufficiently similar to nhTCP, or any portion thereof, such that the nucleic acid molecules are able to form stable hybrids under stringent hybridization conditions with nhTCP.

Preferred nucleic acid molecules are able to form stable hybrids under stringent hybridization conditions with at least one of the following nucleic acid molecules: $nhTCP_{483}$ and $nhTCP_{-2400}$. The production of $nhTCP_{-2400}$ is described in the Examples as is the determination of certain nucleic acid sequences for $nhTCP_{-2400}$ which include SEQ ID NO:3, the deduced amino acid sequence of which is presented herein as SEQ ID NO:4; SEQ ID NO:12, the deduced amino acid sequence of which is presented herein as SEQ ID NO:13; and SEQ ID NO:14, the deduced amino acid sequence of which is presented herein as SEQ ID NO:15. Preferred nucleic acid molecules are capable of hybridizing under stringent conditions with a nucleic acid molecule that includes the nucleic acid sequence SEQ ID NO:1, SEQ ID NO:3, SEQ ID NO:12 and/or SEQ ID NO:14. More preferred nucleic acid molecules include regions that are at least about 86 percent identical, more preferably at least about 90 percent identical, even more preferably at least about 93 percent identical, and even more preferably at least about 95 percent identical with SEQ ID NO:1, SEQ ID NO:3, SEQ ID NO:12, and/or SEQ ID NO:12. Even more preferred are nucleic acid molecules that include the nucleic acid sequence presented in SEQ ID NO:1, SEQ ID NO:3, SEQ ID NO:12, and/or SEQ ID NO:14.

A particularly preferred nucleic acid molecule of the present invention includes at least a portion of nhTCP that is capable of hybridizing under stringent conditions with nhTCP. Examples of such nucleic acid molecules include, but are not limited to, $nhTCP_{483}$, $nhTCP_{-2400}$ and nhTCP.

All of the foregoing nucleic acid molecules can have the characteristic of being a nucleic acid molecule capable of hybridizing to a nucleic acid molecule that encodes a protein that includes the amino acid sequence presented in SEQ ID NO:2, SEQ ID NO:4, SEQ ID NO:13, and/or SEQ ID NO:15. Certain preferred nucleic acid molecules include a nucleic acid molecule that encodes a protein that includes a region that shares at least about 96 percent amino acid sequence identity with SEQ ID NO:2 or a nucleic acid molecule that encodes a protein that includes a region that shares at least about 89 percent amino acid sequence identity with SEQ ID NO:15. More preferred nucleic acid molecules encode at least a portion of a protein having the amino acid sequence of SEQ ID NO:2, SEQ ID NO:4, SEQ ID NO:13 and/or SEQ ID NO:15. Particularly preferred nucleic acid molecules are capable of encoding a protein having dibasic amino acid processing endoprotease activity.

The present invention also includes use of nucleic acid molecules that are oligonucleotides capable of hybridizing, under stringent conditions, with complementary regions of other, preferably longer, nucleic acid molecules of the present invention, such as to complementary regions of CD4+ T-lymphocyte protease genes of the present invention, such as nhTCP. Such oligonucleotides can hybridize under stringent conditions with complementary regions of $nhTCP_{483}$ and/or $nhTCP_{-2400}$; complementary regions of nucleic acid molecules that include at least a portion of $nhTCP_{483}$ and/or $nhTCP_{-2400}$; and complementary regions of nucleic acid molecules that hybridize under stringent conditions with of $nhTCP_{483}$ and/or $nhTCP_{-2400}$. Such oligonucleotides can be RNA, DNA, or derivatives of either. The minimal size of such oligonucleotides is the size required to form a stable hybrid between a given oligonucleotide and the complementary sequence on another nucleic acid molecule of the present invention. As such, the size is dependent on nucleic acid composition and percent identity between the oligonucleotide and complementary sequence as well as upon hybridization conditions per se (e.g., temperature, salt concentration). The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit dibasic amino acid processing endoprotease activity, which be discussed in more detail below.

Knowing the nucleic acid sequence of certain nucleic acid molecules of the present invention allows one skilled in the art to make copies of those nucleic acid molecules as well as to obtain nucleic acid molecules including at least a portion of such nucleic acid molecules and other nucleic acid molecule homologues. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Such libraries, or DNA samples, can include genomic or cDNA, the latter of which can be produced from RNA of any cell type that expresses nhTCP or a homologue thereof. Techniques to clone and amplify genes are disclosed, for example, in Sambrook et al., ibid.

One embodiment of the present invention is a method to identify a gene encoding a cellular animal or plant dibasic amino acid processing endoprotease using a Kex2 endoprotease-deficient yeast strain, which is described in more detail below. A *Saccharomyces cerevisiae* Kex2 endoprotease-deficient yeast strain has been previously used to identify the *S. cerevisiae* KEX2 gene (see, for example, Julius et al., 1984, *Cell* 37, 1075–1089. According to the present invention, a gene encoding an animal or plant dibasic amino acid processing endoprotease can be identified by a method including the steps of (a) transforming a Kex2 endoprotease-deficient yeast strain with a cDNA library prepared from RNA isolated from the desired animal or plant cell type, (b) isolating a transformed yeast strain having a functional dibasic amino acid processing endoprotease as determined, for example, by the ability of such a transformed yeast to form a clear zone in an α-factor zone-clearing assay, and (c) recovering from the transformed yeast the cDNA that includes a gene encoding the desired cellular protease. This method can preferably be used to identify genes that encode cellular proteases responsible for cleavage of precursor viral envelope proteins, such as HIV gp160 precursor proteins. As such, this method can be used to isolate the CD4+ T-lymphocyte dibasic amino acid processing endoprotease that cleaves HIV gp160 precursor proteins. The method can also include the use of a yeast strain that produces a heterologous precursor protein to identify a gene that encodes the dibasic amino acid processing endoprotease that cleaves that protein. Also included in the present invention are dibasic amino acid processing protease genes identified using this method and the proteins such genes encode. A similar method can be used to characterize a nucleic acid molecule that apparently encodes a functional dibasic amino acid processing endoprotease by transforming that nucleic acid molecule into a Kex2 endoprotease-deficient yeast strain such that the protein encoded by the nucleic acid molecule can be expressed and determining whether that protein has proteolytic activity by, for example, determining whether the transformed yeast strain forms a clear zone in an α-factor zone-clearing assay.

One embodiment of the present invention is an isolated protein encoded by a nucleic acid molecule of the present invention. The present invention also includes use of proteins encoded by nucleic acid molecules that can be used in accordance with the present invention as disclosed herein. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source. Examples of such sources are disclosed herein. An isolated protein of the present invention can also be produced using recombinant DNA technology or chemical synthesis.

As used herein, an isolated protein of the present invention can be a full-length dibasic amino acid processing endoprotease encoded by a nucleic acid molecule that forms a hybrid with nhTCP under stringent hybridization conditions. Such a full-length protein is also referred to herein as TCP, or CD4+ T-lymphocyte dibasic amino acid processing endoprotease, an example of which includes hTCP, for human CD4+ T-lymphocyte dibasic amino acid processing endoprotease (although it is to be appreciated that such proteins can also be expressed in other cell types). Additional proteins of the present invention include homologues of TCP, such as a TCP in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue has dibasic amino acid processing endoprotease activity and/or is encoded by a nucleic acid molecule that is capable of hybridizing under stringent conditions with nhTCP. In one embodiment, a homologue also includes at least one epitope capable of eliciting an immune response against a TCP (i.e., when a TCP homologue is administered to an animal as an immunogen, using techniques known to those skilled in the art, the animal will produce a humoral and/or cellular immune response against at least one epitope of the TCP). Dibasic amino acid processing endoprotease activity as well as the ability of a protein to effect an immune response, can be measured using techniques known to those skilled in the art.

TCP homologues of the present invention can be the result of natural allelic variation or natural mutation. TCP homologues can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to cleave dibasic amino acid processing sites and/or to be encoded by a nucleic acid molecule that hybridizes under stringent conditions with nhTCP. Such techniques are known to those skilled in the art.

The minimum size of a protein of the present invention is a size that is sufficient to have been encoded by a nucleic acid molecule capable of hybridizing under stringent conditions with nhTCP. The minimum size of such a protein is from about 4 to about 6 amino acids.

Proteins of the present invention preferably have dibasic amino acid processing endoprotease activity (also referred to herein as dibasic amino acid processing endoproteases) and are able to cleave (i.e., effect cleavage of) a precursor protein having a dibasic amino acid processing site. Sources of such precursor proteins include viruses, bacteria, fungi, animals and plants. A number of such precursor proteins are known to those skilled in the art, including, but not limited to, those disclosed in Barr, ibid. The present invention also includes the ability to identify other precursor proteins that have dibasic amino acid processing sites using techniques known to those skilled in the art, such as cleavage assays and/or amino acid sequence analysis.

Preferred dibasic amino acid processing endoproteases of the present invention are capable of effecting cleavage of precursor proteins of infectious agents that require cleavage of certain precursor proteins in order to be infective. Such infectious agents, therefore, are susceptible to inhibition of dibasic amino acid processing endoprotease activity and can include viruses, bacteria and parasites, with enveloped viruses being preferred. Examples of such viruses include, but are not limited to, retroviruses, herpes viruses, hepadnaviruses, pox viruses, orthomyxoviruses, paramyxoviruses, rhabdoviruses, togaviruses, arena viruses, bunyaviruses and coronaviruses. Preferred dibasic amino acid processing endoproteases of the present invention can effect cleavage of one or more retroviral, herpes viral, and/or hepatitis viral precursor envelope proteins.

Particularly preferred proteins of the present invention are capable of effecting cleavage of a precursor envelope protein of a virus that can infect cells displaying CD4+ markers on their cell surfaces, such as CD4+ T-lymphocytes, macrophages, dendritic cells, reticular cells of the lymph nodes, spleen and thymus, and lymphoid tissue, including Peyer's patches. Preferred viruses to target include lentiviruses and lymphotropic virus that can infect a variety of animals, including, but not limited to, humans, apes, cats, dogs, cattle and other mammals. Examples of such viruses include, but are not limited to, human (HIV), simian (SIV), feline (FIV) and canine (CIV) immunodeficiency viruses, as well as human T-cell lymphotropic virus (HTLV), bovine leukemia virus (BLV) and feline leukemia virus (FLV).

One embodiment of the present invention is a dibasic amino acid processing cleavage of a precursor cellueffect cleavage of a precursor cellular protein that has a dibasic amino acid processing site. As used herein, a cellular protein is a protein that is produced endogenously (i.e., naturally) by a cell. Examples of such precursor cellular proteins include, but are not limited to, precursors of cytokines, hormones, other growth factors, and other factors that regulate the behavior of a cell, such precursors requiring cleavage by a dibasic amino acid processing endoprotease as part of their maturation process.

As discussed above, the extent of cleavage that a particular dibasic amino acid processing endoprotease can effect is a function of the amino acid sequence of the dibasic amino acid processing site and of the dibasic amino acid processing endoprotease. In a preferred embodiment, a dibasic amino acid processing endoprotease of the present invention is selected that can cleave a certain precursor protein with acceptable efficiency, such as selecting hTCP to cleave a HIV precursor envelope gp160 protein.

Proteins of the present invention include proteins encoded by nucleic acid molecules of the present invention as disclosed herein. Preferred proteins include proteins encoded by preferred nucleic acid molecules as disclosed herein. In one embodiment, a preferred protein of the present invention includes an amino acid sequence having at least about 96 percent identity with the amino acid sequence of SEQ ID NO:2 and/or at least about 89 percent amino acid sequence identity with SEQ ID NO:15.

Particularly preferred is a protein that includes an amino acid sequence comprising at least a portion of SEQ ID NO:2, of SEQ ID NO:4 of SEQ ID NO:13 and/or of SEQ ID NO:15, wherein the minimum length of the portion is sufficiently long such that it is encoded by a nucleic acid molecule capable of hybridizing under stringent conditions with nhTCP. Examples of such proteins include, but are not limited to hTCP (encoded by nhTCP), hTCP$_{161}$ (encoded by nhTCP$_{483}$) and nhTCP$_{-800}$ (encoded by nhTCP$_{-2400}$).

The present invention includes fusion proteins comprising a protease protein domain (e.g., TCP or a homologue thereof) attached to a heterologous fusion segment, which preferably comprises one or more amino acids. Inclusion of a fusion segment as part of a protein of the present invention can enhance the protein's stability during production, storage and/or use. Furthermore, a fusion segment can function as a tool to simplify purification of a protein of the present invention, such as to enable purification of the resultant fusion protein using affinity chromatography. In one embodiment, a fusion protein of the present invention can be a multivalent, or multifunctional, protein that includes a proteolytic domain fused to another functional domain. Examples of such multifunctional proteins include, but are not limited to, proteins having more than one enzymatic activity and proteins that include a protease domain and a targeting domain that can target the protease to a desired cell type or to a particular compartment within a cell. The present invention also includes fusion proteins comprising inhibitors of proteases of the present invention joined to targeting domains.

A suitable fusion segment can be a domain of any size that has the desired function. It is within the scope of the present invention to use one or more fusion segments. Fusion segments can be joined to amino and/or carboxyl termini of the protease protein-containing domain of the protein. Linkages between fusion segments and protease protein domains of fusion proteins can be susceptible to cleavage in order to enable straight-forward recovery of the protease protein domains of such proteins. Fusion proteins are preferably produced by culturing a recombinant cell transformed with a fusion nucleic acid molecule that encodes a protein including the fusion segment attached to either the carboxyl and/or amino terminal end of a protease protein-containing domain.

Additional fusion proteins of the present invention include decoy targets that comprise a dibasic amino acid processing site. Exposure of a dibasic amino acid processing endoprotease to such targets reduces the ability of the protease to cleave other proteins. Also included in the present invention are fusion proteins that comprise a marker protein joined to another compound by a dibasic amino acid processing site. Such fusion proteins can be used to assay protease activity if the marker protein is "activated" upon cleavage of the processing site. An example of such a fusion protein is a mature α-factor mating pheromone joined by a dibasic amino acid processing site to another compound such that the α-factor is only active when cleaved from the other compound.

The present invention also includes mimetopes of proteins of the present invention. In accordance with the present invention, a mimetope of a protein refers to any compound that is able to mimic the activity of that protein, often because the mimetope has a structure that mimics the protein. For example, a mimetope of a dibasic amino acid processing endoprotease of the present invention is a compound that has an activity similar to that of an isolated dibasic amino acid processing endoprotease of the present invention. As such, mimetopes of the present invention can be used in a number of applications disclosed herein for proteins of the present invention.

A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using, for example, antibodies raised against a protein of the present invention.

The present invention also includes isolated antibodies capable of selectively binding to a protein of the present invention or to a mimetope thereof. Antibodies capable of selectively binding to a TCP, or homologue thereof, of the present invention are referred to as anti-TCP antibodies. A particularly preferred antibody of this embodiment is an anti-hTCP antibody. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to specified proteins and mimetopes thereof of the present invention. Binding can be measured using a variety of methods known to those skilled in the art, including immunoblot assays, immunoprecipitation assays, radioimmunoassays, enzyme immunoassays (e. g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as reagents in assays to detect and selectively bind to proteins of the present invention; (b) as tools to recover desired proteins of the present invention from a mixture of proteins and other contaminants; (c) as protease inhibitors; and/or (d) as delivery vehicles into a cell. For example, antibodies of the present invention can be produced that selectively bind to and thereby inactivate proteases of the present invention by, for example, direct interaction with the active site of the protease and/or by allosteric interaction with the protease. Antibodies can also deliver inhibitory compounds to a targeted protease. Antibodies of the present invention that are used therapeutically can enter a desired cell type by endocytosis and thereby interact with the catalytic and/or luminal domains of the targeted protease.

The present invention also includes a recombinant vector, which includes a nucleic acid molecule of the present invention inserted into any vector capable of delivering the nucleic acid molecule into a host cell. Such a vector contains heterologous nucleic acid sequences, that is nucleic acid sequences that are not naturally found adjacent to nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Any nucleic acid molecule disclosed herein can be included in a recombinant vector of the present invention. Preferred nucleic acid molecules to include are preferred nucleic acid molecules of the present invention.

In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable, as well as preferred, nucleic acid molecules with which to transform a host cell are provided herein.

Suitable host cells to transform include any cell that can be transformed and that can express the introduced nucleic acid molecule(s). Such cells are, therefore, capable of producing proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect, mammalian and amphibian (e.g., Xenopus) cells.

A recombinant cell is preferably produced by transforming a host cell with one or more recombinant molecules, each comprising one or more nucleic acid molecules of the present invention operatively linked to one or more transcription control sequences, preferably included within an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Also preferred are expression vectors that can integrate into the host genome.

Expression vectors can be either prokaryotic or eukaryotic, and are typically viruses or plasmids. Expression vectors of the present invention include any vectors that function (i.e., direct gene expression) in recombinant cells of the present invention, including in bacterial, fungal (including yeast), insect, animal, and/or plant cells. As such, nucleic acid molecules of the present invention can be operatively linked to expression vectors containing regulatory sequences such as promoters, operators, repressors, enhancers, transcription termination sequences, sequences that regulate translation, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and/or repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect, mammalian, and/or amphibian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, yeast α-factor mating pheromone, yeast formate dehydrogenase, Pichia alcohol oxidase, viral long terminal repeat, other mammalian viral, insect viral, or subtilisin-like protein convertase transcription control sequences as well as other sequences capable of controlling gene expression in prokaryotic or eukaryotic cells. Additional yeast promoters include, but are not limited to promoters of genes encoding the following yeast proteins: Kex2, alcohol dehydrogenase I (ADH1) or II (ADH2), phosphoglycerate kinase (PGK), triose phosphate isomerase (TPI), glyceraldehyde-3-phosphate dehydrogenase (GAPDH; also referred to as TDH3, for triose phosphate dehydrogenase), galactokinase (GAL1),galactose-1-phosphateuridyl-transferase (GAL7), UDP-galactose epimerase (GAL10), cytochrome $c_1$ (CYC1) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in yeast include, but are not limited to, the UASs of genes encoding the following proteins: CYC1, ADH2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in yeast include the termination sequences of the α-factor mating pheromone, GAPDH, and CYC1 genes. Transcription control sequences of the present invention can also include naturally occurring transcription control sequences naturally associated with a DNA sequence encoding a dibasic amino acid processing endoprotease protein of the present invention.

Recombinant molecules of the present invention may also contain secretory signals (i.e., signal segment nucleic acid sequences) to enable an expressed protein to enter into the secretory pathway in the cell that produces the protein. Suitable signal segments can be determined by those skilled in the art.

Recombinant molecules of the present invention may also contain fusion sequences which lead to the expression of inserted nucleic acid molecules of the present invention as fusion proteins, examples of which are disclosed herein.

A recombinant molecule of the present invention includes at least one of any nucleic acid molecule heretofore described operatively linked to at least one of any transcription control sequence capable of effectively regulating expression of the nucleic acid molecule(s) in the cell to be transformed. Suitable and preferred nucleic acid molecules to include in recombinant molecules of the present invention are disclosed herein. Particularly preferred recombinant molecules include the following regulatory sequences: TDH3 or ADH2/GAPDH promoter sequences, Kex2 or α-factor mating pheromone signal and leader sequences, a translation stop sequence, and CYC1 or α-factor mating pheromone transcription terminator sequences. Even more preferred recombinant molecules include pα/nhTCP$_{-2400}$ and pα/nhTCP, the production of which is described in the Examples section.

A recombinant cell of the present invention includes any cell that is transformed with at least one of any nucleic acid molecule of the present invention. Suitable and preferred nucleic acid molecules and recombinant molecules with which to transform cells are disclosed herein. Particularly preferred recombinant cells include S. cerevisiae CB023:pα/nhTCP$_{-2400}$, S. cerevisiae CB023:pα/nhTCP and S. cerevisiae kex2Δ:pα/env,pα/nhTCP, the production of which is described in the Examples section.

It may be appreciated by one skilled in the art that use of recombinant DNA technologies can improve expression of transformed nucleic acid molecules by manipulating, for example, the number of copies of the nucleic acid molecules within a host cell (e.g., by using cir° strains), the efficiency with which those nucleic acid molecules are transcribed, the efficiency with which the resultant transcripts are translated, the efficiency of post-translational modifications, and the ability to maintain plasmids within a cell (e.g., by incorporating a selectable marker, such as an antibiotic resistance or prototrophic gene, on the plasmid). Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce a protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a protein of the present invention. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant proteins may either remain within the recombinant cell; be secreted into the fermentation medium; be secreted into a space between two cellular barriers (e.g., cell membranes and/or cell walls), such as the periplasmic spaces of E. coli and yeast; or be retained on the outer surface of a cell or viral (including bacteriophage) membrane. The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

In one embodiment, dibasic amino acid processing endoprotease proteins of the present invention are retrieved in "substantially pure" form. As used herein, "substantially pure" refers to a purity that allows for the effective use of the protein, for example, to identify an inhibitor thereof, as disclosed in more detail herein.

In another embodiment, dibasic amino acid processing endoprotease proteins of the present invention are retained within the recombinant cells that produced them. Such recombinant cells can have a variety of uses including in delivery and assay systems.

One embodiment of the present invention is a recombinant cell comprising a cell transformed with, and capable of expressing, a first nucleic acid molecule that is capable of hybridizing, under stringent conditions, with a dibasic amino acid processing endoprotease gene comprising nhTCP. Such a recombinant cell can be used in the production of proteins of the present invention and in a variety of other applications disclosed herein, including, but not limited to, the identification of compounds that inhibit dibasic amino acid processing endoproteases of the present invention and the production of surrogate cells that produce desired proteins. Preferred proteins have dibasic amino acid processing endoprotease activity. In one embodiment, such a recombinant cell can be a cell transformed in vivo, ex vivo or in vitro with a nucleic acid molecule that reduces dibasic amino acid processing endoprotease activity in the transformed cell compared to in an untransformed cell, as a result of, for example, anti-sense, triplex-helix formation, gene knockout, and/or RNA drug based technologies.

In one embodiment, a recombinant cell capable of expressing a dibasic amino acid processing endoprotease protein of the present invention also produces a precursor protein having a dibasic amino acid processing site. The precursor protein can be either an endogenous or heterologous precursor protein. An endogenous protein is naturally produced by the cell, whereas a heterologous precursor protein is encoded by a second nucleic acid molecule that has been introduced into the recombinant cell. Such recombinant cells can be used in a variety of applications including, but not limited to, identification of compounds that inhibit dibasic amino acid processing endoproteases of the present invention and surrogate producers of desired proteins.

Recombinant cells of the present invention can be produced in vitro or in vivo. That is, nucleic acid molecules can be introduced into cells (i.e., transformation can occur) either in vitro or in vivo.

The present invention includes therapeutic compositions that are capable of reducing the infectivity of an infectious agent that has a dibasic amino acid processing site. Such compositions are based on the discovery of the human T cell protease gene and, as such, can be targeted to TCPs and homologues thereof. Such compositions include, but are not limited to, nucleic acid molecules capable of hybridizing under stringent conditions with a dibasic amino acid processing endoprotease gene comprising nhTCP as well as compounds that inhibit dibasic amino acid processing endoprotease activity; such inhibitory compounds can be identified by their ability to inhibit the activity of hTCP. Therapeutic compositions of the present invention can also include other components, such as excipients. Suitable excipients include any component in which nucleic acid molecules, proteins, or inhibitory compounds of the present invention can be formulated that the animal to be treated can tolerate. The use of excipients is well known to those skilled in the art as are suitable excipients themselves.

Therapeutic compositions of the present invention are able to reduce the infectivity of an infectious agent by interfering with the production of one or more cleavage proteins required in the production of an infectious agent. For example, many if not all envelope (or enveloped) viruses produce precursor envelope proteins that require cleavage by dibasic amino acid processing endoproteases in order to propagate infectious virus. One such precursor envelope protein is the HIV gp160. The present invention includes compositions that are capable of reducing the spread of HIV and, thus to retard or reverse the onset of AIDS, because the compositions are capable of blocking the cleavage of gp160 into gp120 and gp41 in T lymphocytes.

Therapeutic compositions of the present invention are capable of reducing, or inhibiting, the propagation or spread of an infectious agent through a host, thereby decreasing or preventing further infection and/or disease otherwise caused by the infectious agent. Infectious agents are capable of spreading through host organisms by infecting cells, replicating and infecting additional cells, often causing disease. Infectious agents include viruses, bacteria, fungi, other parasites, and any other agents that effect infection and disease, particularly in animals and plants, and more particularly in animals. As used herein, susceptible infectious agents are infectious agents that have reduced infectivity when dibasic amino acid processing endoprotease activity is reduced. Examples of susceptible infectious agents are disclosed herein. Preferred infectious agents to target with therapeutic compositions of the present invention are enveloped viruses, such as retroviruses (e.g., lentiviruses, such as immunodeficiency viruses; type A cisternaviruses; type B oncoviruses, such as mammary tumor viruses; type C oncoviruses, such as human lymphotropic viruses, leukemia viruses, sarcoma viruses, leukosis viruses; type D oncoviruses; and type F spumaviruses), herpes viruses (e.g., cytomegaloviruses, herpes simplex, varicella-herpes zoster, and Epstein-Barr viruses), hepadnaviruses (e.g., hepatitis A, B, C, D, E, and other non-A, non-B hepatitis viruses), poxviruses (e.g., variola and vaccinia viruses), orthomyxoviruses (e.g., influenza viruses), paramyxoviruses (e.g., measles, mumps, para influenza, Sendai and Newcastle disease viruses), rhabdoviruses (e.g., filoviridae, rabies and vesicular stomatitis virus), togaviruses (e.g. flaviviruses and alphaviruses), arena viruses, bunyaviruses and coronaviruses. Retroviruses, herpes viruses, and hepatitis viruses are more preferred infectious agents to target, with leukemia, lymphotropic, sarcoma and lentiviruses being even more preferred, and with viruses capable of infecting a cell type expressing CD4+ markers being especially preferred. Particularly preferred lymphotropic viruses include HTLVs, such as HTLV-I and HTLV-II; BLVs; and FLVs. Particularly preferred lentiviruses include HIV, SIV, FIV, and CIV, with HIV-1 and HIV-2 being even more preferred.

One embodiment of the present invention is a therapeutic composition that includes a nucleic acid molecule that is capable of hybridizing under stringent conditions with a dibasic amino acid processing endoprotease gene comprising nhTCP. The size of such a nucleic acid molecule is restricted only in that the molecule must be capable of forming a hybrid as stated. As such, nucleic acid molecules included in therapeutic compositions can be oligonucleotides, full-length genes, or partial genes and can correspond to regulatory and/or coding regions of protease genes. Such nucleic acid molecules, examples of which are disclosed herein, can be administered in an effective manner to decrease production of dibasic amino acid processing endoproteases within cells using, for example, antisense-, triplex formation-, ribozyme-, gene knockout- and/or RNA drug-based technologies. The present invention, therefore, includes such nucleic acid molecule-containing therapeutic compositions and methods to interfere with the production of dibasic amino acid processing endoproteases by use of one or more of such technologies. Appropriate nucleic acid molecule-containing therapeutic compositions can be administered to an animal, using techniques known to those skilled in the art, either prior to or after infection by an infectious agent in order to protect the animal from disease.

Another embodiment of the present invention is a therapeutic composition that includes an inhibitory compound that inhibits dibasic amino acid processing endoprotease activity. Such a compound can be identified by its ability to inhibit the activity of hTCP or of a homologue or mimetope thereof. Also included are methods to identify such inhibitory compounds, yeast strains that can be used to identify inhibitory compounds method and assay kits based on such methods.

The use of compounds that inhibit dibasic amino acid processing endoproteases of the present invention as therapeutic compounds have several advantages. Cellular dibasic amino acid processing endoproteases are preferred over enzyme targets inherent to the infectious agent (e.g., polymerases, regulatory factors, surface antigens, or proteases encoded by the infectious agent) because it is believed that over time, drug-resistant infectious agents are likely to develop much more rapidly than are drug-resistant cellular proteases. Cellular dibasic amino acid processing endoproteases are also attractive targets for inhibitory drug therapy because the cellular location of dibasic amino acid processing endoproteases in the secretory pathway (often in or near the Golgi apparatus) causes dibasic amino acid processing endoproteases to be susceptible to compounds that are endocytosed by cells. As such, inhibitory drug compounds can be of any substance capable of being endocytosed including compounds that are at least partially, and preferably essentially completely, soluble in an aqueous (hydrophilic) solution. That is, inhibitory compounds of the present invention do not need to be lipophilic as the compounds need not cross cell membranes if "delivered" by endocytosis. Furthermore, inhibitors of cellular dibasic amino acid processing endoproteases are less likely to cause severe side effects since reductions in cellular dibasic amino acid processing endoprotease activity apparently are not significantly harmful to the cell. For a more detailed discussion, see Ser. No. 08/088,322, ibid.

In accordance with the present invention, a yeast-based assay such as that disclosed in Ser. No. 08/088,322, ibid., can be used to identify compounds that are capable of inhibiting the activity of dibasic amino acid processing endoprotease proteins of the present invention (e.g., TCPs and homologues thereof). Yeast strains possess a dibasic amino acid processing endoprotease located in the Golgi apparatus called Kex2 endoprotease that is capable of processing (i.e., cleaving) yeast precursor proteins having dibasic amino acid processing sites, such as precursor proteins for α-factor mating pheromones and killer toxins. Yeast strains lacking a functional Kex2 endoprotease can grow normally; such strains, however, are unable to mate and show reduced functions at low growth temperatures (i.e., at less than about 14° C.). Apparently all wild-type yeast strains, regardless of genus or species, produce a protease having Kex2-type activity (i.e., a Kex2 endoprotease) since all wild-type yeast strains apparently are capable of mating. As used herein, the phrases a "yeast strain lacking a functional Kex2 endoprotease" and a "Kex2 endoprotease-deficient yeast strain" each refer to a yeast strain in which the Kex2 endoprotease is either absent or modified such that the enzyme has essentially no proteolytic activity (i.e., less than about 10 percent, preferably less than about 5 percent, and more preferably less than about 1 percent of wild-type Kex2 endoprotease activity). As such, a Kex2 endoprotease-deficient strain is essentially unable to produce mature α-factor mating pheromones unless the strain is supplemented with a functional dibasic amino acid processing endoprotease, for example, by transforming the strain with a gene encoding a functional dibasic amino acid processing endoprotease, such as with a nucleic acid molecule of the present invention that encodes a protein having dibasic amino acid processing endoprotease activity.

One embodiment of the present invention is a method to identify a compound that inhibits proteolytic cleavage by a dibasic amino acid processing endoprotease of the present invention (i.e., a dibasic amino acid processing endoprotease that is encoded by a nucleic acid molecule of the present invention). The method includes the steps of (a) contacting a Kex2 endoprotease-deficient yeast strain that is transformed with a nucleic acid molecule of the present invention and that contains a precursor protein having a dibasic amino acid processing site with a putative inhibitory compound under conditions in which, in the absence of the compound, the yeast strain is capable of effecting cleavage of the precursor protein into cleavage products; and (b) assaying for production of at least one of the cleavage products. Production of a reduced amount of a (i.e., at least one) cleavage product in the presence of the putative inhibitory compound compared to in the absence of the putative inhibitory compound indicates that the compound is able to inhibit proteolytic cleavage by the endoprotease. The precursor protein can be either a yeast precursor protein or a heterologous precursor protein. In the instance of a system based on cleavage of a yeast precursor protein, the ability of the putative inhibitory compound to inhibit the cleavage of the yeast precursor protein is indicative of (positively correlates with) the ability of the putative inhibitory compound to inhibit the cleavage of a heterologous precursor protein; see Ser. No. 08/088,322, ibid. An advantage of using a Kex2 endoprotease-deficient strain expressing a dibasic amino acid processing endoprotease of the present invention is that such a method identifies compounds that interact with the endoprotease with high affinity and specificity without affecting cell viability. For example, a particularly preferred yeast strain to use to identify compounds that inhibit HIV infection is a Kex2 endoprotease-deficient *S. cerevisiae* strain that expresses hTCP. Other suitable and preferred dibasic amino acid processing endoproteases, as well as other suitable and preferred precursor proteins are disclosed herein.

The term yeast precursor protein refers to a precursor protein of the same species as the yeast strain used in the identification of inhibitory compounds in accordance with the present invention. Yeast precursor proteins are preferably produced endogenously by the yeast strain. Any yeast precursor protein having a dibasic amino acid processing site, the cleavage of which can be detected, can be monitored to determine whether the putative inhibitory compound can inhibit the ability of a dibasic amino acid processing endoprotease to cleave a heterologous precursor protein. Suitable yeast precursor proteins include, but are not limited to precursor proteins of α-factor mating pheromones and killer toxins. A preferred yeast precursor protein to monitor is a precursor α-factor protein.

The phrases a precursor protein heterologous to a yeast precursor protein and a heterologous precursor protein each refer to a precursor protein that is naturally produced in a cell type other than the yeast strain used in the identification of inhibitory compounds in accordance with the present invention or that is produced synthetically and has a sequence that is not identical to a homologous yeast precursor protein. The heterologous precursor protein can be, for example, a precursor protein of an infectious agent or a labeled precursor protein that can be used as a marker in the method to identify compounds that inhibit dibasic amino acid processing endoproteases. A heterologous precursor protein can be a precursor α-factor protein that has a heterologous dibasic amino acid processing site, such as the processing site of an infectious agent. A heterologous precursor protein can be produced by a yeast strain of the present invention by genetically engineering the yeast strain to produce the protein, using recombinant techniques known to those skilled in the art to insert the gene encoding the protein into the yeast strain in a manner such that the yeast strain is capable of expressing (i.e., producing) the precursor protein (see, for example, Sambrook et al., *Molecular Cloning: A Laboratory Manual*, Cold Spring Harbor Labs Press, 1989; Pichuantes et al., in *Principles and Practice of Protein Engineering*, Wiley and Sons, 1995, in press, Cleland and Craik, eds.). Suitable and preferred heterologous precursor proteins are disclosed herein and in Ser. No. 08/088,322, ibid.

The use of a yeast-based assay in the present invention, particularly as an initial screen, to identify compounds that inhibit dibasic amino acid processing endoproteases of the present invention has several advantages. As a eukaryote, yeast have subcellular organelles and are able to perform many post-translational modifications in a manner similar to that effected by mammalian cells, such as N-terminal myristylation, prenylation, acetylation, phosphorylation, removal of N-terminal methionine, N- and O-linked glycosylation, disulfide bridge formation and protein oligomerization. Like bacteria, yeast are easy to manipulate both genetically and biochemically, easy to transform, grow rapidly (doubling times of about 1.5 to about 4 hours) on inexpensive medium, and produce heterologous proteins in large quantities. Thus, a yeast-based assay is less complicated, less expensive, and less time-consuming than an animal cell-based assay for the identification of inhibitory compounds. A number of putative inhibitory compounds can be screened in a rapid manner, either as pools of compounds or individually. Furthermore, a yeast-based assay to identify inhibitors of dibasic amino acid processing endoproteases that otherwise would enable propagation and spread of infectious agents obviates the need to work with live infectious agents to identify such inhibitory compounds. In addition, yeast can be genetically and recombinantly manipulated in a straight-forward manner to obtain strains that produce dibasic amino acid processing endoproteases of the present invention as well as yeast and/or heterologous precursor proteins. Use of yeast strains that lack a functional yeast Kex2 endoprotease but that can express a dibasic amino acid processing endoprotease of the present invention reduces potential interference by other cellular components being expressed by the cell type that endogenously produces the particular dibasic amino acid processing endoprotease.

Suitable yeast strains to use in the present invention include any Kex2 endoprotease-deficient yeast strain that can be transformed to produce a dibasic amino acid processing endoprotease of the present invention. The yeast can be haploid, diploid, or polyploid. Yeasts with higher ploidy typically exhibit less deleterious mutation effects. Preferred yeast strains include strains of the genera Saccharomyces, Pichia, Hansenula, Schizosaccharomyces, Kluyveromyces, Yarrowia and Candida. Preferred species include *Saccharomyces cerevisiae, Pichia pastoris, Hansenula polymorpha, Schizosaccharomyces pombe, Kluyveromyces lactis, Yarrowia lipolytica* and *Candida maltosa*. *S. cerevisiae* strains are particularly preferred because of the versatility of such strains including the ease with which such strains can be manipulated genetically and recombinantly, the ease with which such strains can be cultured and induced to produce heterologous proteins, and the variety of strains available for use. Kex2 endoprotease-deficient yeast strains can be produced using a variety of methods known to those skilled in the art, preferably by genetic modification. A preferred genetic method to produce a Kex2 endoprotease-deficient strain is gene replacement (see, for example, Fuller et al., 1989, *Science* 246, 482–486; and Franzusoff et al., 1991, *J. Cell. Biol.* 112, 27–37). Recombinant methods to produce yeast strains for use in identifying inhibitor compounds are disclosed herein and in Ser. No. 08/088,322.

One embodiment of the present invention is a Kex2 endoprotease-deficient yeast strain that is transformed with a nucleic acid molecule of the present invention. The nucleic acid molecule preferably encodes an active dibasic amino acid processing endoprotease. Such a strain has particular utility in assay methods and test kits of the present invention. Preferred strains are also transformed with a heterologous precursor protein that can be cleaved by the heterologous dibasic amino acid processing endoprotease produced by the yeast strain.

The conditions under which the yeast strain is contacted with (e.g., mixed with, exposed to) the putative inhibitory compound are conditions in which the yeast strain can normally cleave a precursor protein having a dibasic amino acid processing site if essentially no inhibitor is present. Such conditions include an effective medium in which the yeast strain can be cultured such that the dibasic amino acid processing endoprotease produced by the yeast can exhibit biological activity (i.e., is capable of cleaving precursor proteins). Such conditions are disclosed in Ser. No. 08/088, 322, ibid.

The present invention includes any of a variety of methods to determine if putative inhibitory compounds contacted with the yeast strain can inhibit cleavage of a yeast or heterologous precursor protein, including in vivo plate assays, such as α-factor zone clearing, or halo, assays, mating assays, and killer toxin halo assays; methods to separate precursor and cleavage proteins, such as centrifugation, chromatography, electrophoresis, filtration and chemical modification (e.g., biotinylation to detect presence of cleavage protein on cell surface); methods to directly measure cleavage (e.g., use of fluorigenic peptides which emit fluorescent light when cleaved); and antibody-based methods to detect and discriminate between precursor and cleavage proteins, such as immunoprecipitation followed by gel electrophoresis and immunoblot assays. Another method to detect cleavage is to culture yeast spheroplasts, in which case cleaved proteins are secreted into the medium, which can be analyzed by enzyme immunoassay (e.g., ELISA) or radioimmunoassay. Antibodies that selectively bind to a given precursor protein or its cleaved product can be produced using standard techniques, or purchased when available. Antibodies against an infectious agent can be isolated from the infected animal's serum. In one embodiment, secretion of cleaved proteins into the culture medium is detected using a dipstick assay in which, for example, an antibody raised against the cleaved protein is attached to the dipstick. If cleavage of the precursor protein is critical for syncytium formation (e.g., a precursor retroviral envelope protein), putative inhibitory compounds may be tested for their ability to prevent syncytium formation of envelope protein-expressing yeast spheroplasts with cells expressing receptors for the retrovirus. A number of these methods are described in detail in Ser. No. 08/088,322. A preferred method to use to identify inhibitory compounds is the α-factor zone clearing, or halo, assay. In one embodiment, the precursor α-factor protein is modified to include a heterologous dibasic amino acid processing site most preferred by the dibasic amino acid processing endoprotease being tested.

Another embodiment of the present invention is an in vitro method to identify a compound that inhibits a dibasic amino acid processing endoprotease of the present invention. The method includes the steps of (a) contacting a putative inhibitory compound with a secreted soluble dibasic amino acid processing endoprotease protein of the present invention in the presence of a precursor protein having a dibasic amino acid processing site under conditions in which, in the absence of said compound, the endoprotease protein is capable of effecting cleavage of the precursor protein into cleavage products; and (b) assaying for production of the cleavage products. Production of a reduced amount of cleavage products in the presence of the putative inhibitory compound compared to in the absence of the putative inhibitory compound indicates that the compound is able to inhibit dibasic amino acid processing endoprotease proteolytic cleavage. As used herein, a secreted soluble dibasic amino acid processing endoprotease protein of the present invention is a dibasic amino acid processing endoprotease of the present invention that retains proteolytic activity but that essentially lacks the transmembrane and C-terminal cytosolic domains. As such, the endoprotease protein can be secreted into the culture medium. Such a protein can be produced as described in Ser. No. 08/088,322, ibid. The ability of a putative inhibitory compound to inhibit dibasic amino acid processing endoprotease cleavage can be determined in a variety of ways as heretofore described, including plate assays, methods to separate precursor and cleavage proteins, methods to directly measure cleavage, and antibody-based methods to detect and discriminate between precursor and cleavage proteins.

Another embodiment of the present invention is a method to screen for compounds that inhibit the cleavage of a heterologous precursor protein by a heterologous dibasic amino acid processing endoprotease which includes several screening stages of increasing specificity. Such a method enables one skilled in the art to rapidly select an inhibitory compound of desired specificity from a large group of putative inhibitory compounds. It should be recognized that not all of the following screening stages are required and that one or more stages can be used in a variety of combinations and orders. Suitable stages and combinations thereof are disclosed in Ser. No. 08/088,322.

The present invention includes inhibitory compounds identified by the assay methods of the present invention. The term inhibitory compound refers to a compound that inhibits a dibasic amino acid processing endoprotease. A putative inhibitory compound is a compound that is being tested to determine if it is capable of inhibiting the dibasic amino acid processing endoprotease. The ability of a compound to inhibit a dibasic amino acid processing endoprotease refers to the ability of the compound to reduce the activity of the endoprotease, preferably to the extent that a substantial amount of precursor protein is not cleaved compared to cleavage effected by the endoprotease in the absence of the compound. The inhibition is preferably sufficient to interfere with the ability of an infectious agent that requires cleavage of such a precursor protein to propagate and spread to other cell types; that is, the inhibitor is able to reduce disease progression by the infectious agent. Inhibition of retroviral infection preferably includes reduction in infectivity, syncytium formation, and fusion between infected and uninfected cells.

A preferred inhibitory compound of the present invention is one that is specific for the dibasic amino acid processing endoprotease being targeted but that does not substantially adversely affect other cellular components, including other classes of proteases. That is, the compound can inhibit the targeted dibasic amino acid processing endoprotease with fewer side effects than drugs currently used for treatment, such as nucleoside analogs. Preferred inhibitory compounds are peptides, mimetopes, or mixtures thereof. As used herein, a mimetope is any organic compound that mimics the ability of a peptide to inhibit cleavage by a dibasic amino acid processing endoprotease. Such inhibition can be due to allosteric interactions with the protease as well as direct interactions with the catalytic domain. Mimetopes can be peptides in which the scissile peptide bond is replaced by a bond that cannot be cleaved by the endoprotease, for example by introducing a thio group. Alternatively, mimetopes can be synthetic or natural organic molecules, including nucleic acids, that have a structure similar to the dibasic amino acid processing site and, as such, bind with high affinity to the dibasic amino acid processing endoprotease.

A preferred concentration of the inhibitory compound to use in treatment is less than about 100 micromolar (µM), more preferably in the range of about 1 to about 10 µM and even more preferably in the range of about 1 to about 300 nanomolar (nM), which is the concentration at which apparently useful inhibitors of the HIV-1 encoded aspartyl protease are being administered. Inhibitory compounds delivered in such concentration ranges preferably inhibit at least about 50, and more preferably at least about 65, and even more preferably at least about 75 percent of the activity of the targeted dibasic amino acid processing endoprotease.

The inhibitory compound can effect either permanent or temporary inhibition by, for example, binding, respectively, irreversibly or reversibly to the dibasic amino acid processing endoprotease. The inhibitory compound may also modify the dibasic amino acid processing endoprotease, for example, by chemically inactivating the dibasic amino acid processing endoprotease. For example, an alkylating agent, such as chlorambucil, can be attached to a peptide having a dibasic amino acid processing site or a mimetope of such a peptide.

The inhibitory compound can further include a component that permits targeting of the compound to a particular cell type capable of producing the dibasic amino acid processing endoprotease. Such a component can include any substance that binds selectively to the cell type, such as an antibody, hormone, lymphokine, other ligand, or even a part of a viral envelope protein capable of binding to a receptor on the targeted cell type (e.g., at least a portion of HIV gp120 that can target the CD4 receptor on human CD4+ T-lymphocytes.), or portions thereof that retain binding activity.

One aspect of the present invention is the selection of putative inhibitory compounds to test in accordance with the present invention. Any compound can be tested; however, a preferred method to select putative inhibitory compounds is to follow a strategy similar to that used in identifying other protease inhibitors, such as inhibitors of the HIV-1 encoded aspartyl protease. Such a method and examples of putative inhibitory compounds are disclosed in more detail in Ser. No. 08/088,322, ibid. Putative inhibitory compounds can be tested in pools, using techniques known to those skilled in the art. Putative inhibitory compounds can be produced using techniques known to those skilled in the art.

The present invention also includes test kits to identify a compound capable of inhibiting a dibasic amino acid processing endoprotease of the present invention. Such kits include a Kex2 endoprotease-deficient yeast strain transformed with a nucleic acid molecule that encodes the dibasic amino acid processing endoprotease. The yeast strain also contains a precursor protein having a dibasic amino acid processing site that the yeast strain is capable of cleaving into cleavage products. The test kit also includes a means for determining the extent of cleavage by the yeast strain in the presence of a putative inhibitory compound. The determining means includes means for assaying for production of the cleavage products. Production of a reduced amount of cleavage products in the presence of the putative inhibitory compound compared to in the absence of the putative inhibitory compound indicates that the compound being tested is able to inhibit proteolytic cleavage by the dibasic amino acid processing endoprotease. Any suitable means to determine cleavage, including those heretofore disclosed, can be used. Examples of determining means are disclosed in Ser. No. 08/088,322, ibid.

In a preferred embodiment, test kits of the present invention are used to identify compounds that can inhibit infectious agents and thus treat or prevent disease. A particularly preferred test kit is capable of identifying compounds that reduce the infectivity of HIV. Compounds that are identified by test kits of the present invention as being able to inhibit cleavage of HIV gp160 into gp120 and gp41 can be used to treat HIV infection and to prevent or reduce the occurrence of AIDS.

The methods and test kits of the present invention are particularly useful in developing antiviral drugs that block cleavage of precursor envelope proteins by cellular dibasic amino acid processing endoproteases. One concern of targeting cellular proteases is whether the targeted cells will still function properly if the targeted dibasic amino acid processing endoproteases are inhibited by the antiviral drugs. Without being bound by theory, it is believed that inhibition of dibasic amino acid processing endoproteases will not be substantially harmful to the cells producing the dibasic amino acid processing endoproteases since Kex2 endoprotease-deficient yeast strains and Chinese hamster ovary cells apparently lacking a functional dibasic amino acid processing endoprotease are viable, as disclosed in Ser. No. 08/088,322. It is contemplated, however, that if inhibition of a cellular dibasic amino acid processing endoprotease reduces maturation of a key protein normally processed by that dibasic amino acid processing endoprotease (such as a hormone), the antiviral treatment can be supplemented by such a key protein.

One aspect of the invention is the development of targeted therapies to treat HIV infection and prevent the onset of ARC or AIDS. As such, a preferred therapy is one that is targeted to the human CD4+ T-lymphocyte dibasic amino acid processing endoprotease that naturally cleaves gp160, i.e., hTCP. Thus, a preferred method to prevent the spread of HIV is to (a) identify a compound that inhibits hTCP from cleaving an HIV gp160 precursor protein by (i) contacting putative inhibitory compounds with a Kex2 endoprotease-deficient yeast strain that produces hTCP and (ii) selecting a compound that can reduce cleavage of gp160; and (b) administering the selected compound to a person in need of such a treatment.

The use of a test kit of the present invention in which a CD4+ T-lymphocyte dibasic amino acid processing endoprotease is produced by the yeast strain permits one to identify compounds that bind with high affinity to the correct binding pocket in the CD4+ T-lymphocyte dibasic amino acid processing endoprotease. Such compounds will be particularly useful therapeutics as they should exhibit a high specific activity that permits them to be administered in low dosages. It is also believed that relatively low doses of inhibitory compounds of the present invention will be sufficient for treatment because the relatively low abundance of yeast Kex2 endoprotease in cells and the relatively low activity of human CD4+ T-lymphocyte dibasic amino acid processing endoprotease in cleaving HIV gp160 suggest that cells produce relatively low amounts of dibasic amino acid processing endoproteases.

Targeting cellular dibasic amino acid processing endoproteases in accordance with the present invention permits inhibitory compounds to be delivered to the dibasic amino acid processing endoproteases by endocytosis, as heretofore disclosed. Inhibitory compounds of the present invention can be endocytosed by the cell membrane (fluid phase endocytosis). Alternatively, an inhibitory compound of the present invention can be a conjugate that includes a component that targets the compound to a receptor on a targeted cell type, in which case the compound is internalized by receptor mediated endocytosis.

The present invention also includes prodrugs, and production thereof, that include a dibasic amino acid processing site which are taken up by endocytosis and cleaved by dibasic amino acid processing endoproteases in the Golgi apparatus to produce an active drug. An example of a prodrug of the present invention is an active drug coupled to a positively or negative charged side group in such a manner that a dibasic amino acid processing site is situated between the active drug and the side group. The side group enables the prodrug to be hydrophilic, thereby allowing it to be soluble in bodily fluids and susceptible to endocytosis. After being endocytosed, the prodrug is transferred to the Golgi apparatus where it is cleaved by a dibasic amino acid processing endoprotease. Upon cleavage, the activated drug, if lipophilic, can migrate across the membrane into the cytoplasm of the cell. As such, the activated drug can be targeted against a cytoplasmic agent.

One embodiment of the present invention is a recombinant cell that includes a nucleic acid molecule that encodes a defective dibasic amino acid processing endoprotease protein of the present invention, that is a protein that encodes a dibasic amino acid processing endoprotease protein that has reduced or no dibasic amino acid processing endoprotease activity. Such a recombinant cell can be used in an ex vivo protocol to protect an animal from infection by an infectious agent that infects that cell type. Such a recombinant cell, or the nucleic acid molecule itself, can be used to produce a transgenic animal that has reduced susceptibility to infection by an infectious agent that requires dibasic amino acid processing endoprotease to propagate. The nucleic acid molecule can also be delivered to targeted cells in vitro or in vivo by a number of techniques. A preferred gene delivery technique is disclosed in Ser. No. 08/340,185, ibid.

The present invention also includes therapeutic compositions that can be used to decrease dibasic amino acid processing endoprotease activity in order to reduce excess production of proteins that are derived from precursor proteins, such as cytokines, hormones, other immunoregulatory factors, other growth factors, and other regulatory factors. Such compositions include, but are not limited to, nucleic acid molecules that can reduce production of the proteins themselves or inhibitory compounds that reduce the activity of the dibasic amino acid processing endoproteases involved in maturation of those proteins. Such compositions can be used to immunomodulate an excessive immune response, such as in an autoimmune disease, to decrease the production of factors that stimulate tumor cell growth, or to otherwise modulate autocrine, paracrine, or endocrine function of cells that rely on dibasic amino acid processing endoproteases of the present invention, including CD4+ T-lymphocytes.

The present invention also includes therapeutic compositions that can be used to increase dibasic amino acid processing endoprotease activity. One embodiment of the present invention is a therapeutic composition comprising a nucleic acid molecule of the present invention that encodes an active dibasic amino acid processing endoprotease that can be delivered to a cell in vitro or in vivo in order to increase cleavage of precursor proteins in that cell. The cell to which the nucleic acid molecule is delivered can be a cell type that endogenously produces the dibasic amino acid processing endoprotease or a cell type that normally does not produce that dibasic amino acid processing endoprotease, in which case the cell is referred to as a surrogate. A number of methods can be used for gene delivery. A preferred method is the use of yeast-based delivery vehicles to deliver genes, as disclosed in Ser. No. 08/340,185, ibid. Such therapeutic compositions can be used, for example, to increase cytokine or hormone production, such as insulin production in diabetics or renin production in animal with high blood pressure. In one embodiment, the surrogate cell functions as an implant, or time-release capsule, to release a desired compound at an appropriate rate over time. Surrogate cells can be produced in vivo or can be produced ex vivo and then implanted at a desired site of action.

The present invention also includes a method to protect an animal from disease by administering to the animal a therapeutic composition of the present invention. In accordance with the present invention, the ability of a therapeutic composition of the present invention to protect an animal from disease refers to the ability of that composition to treat, ameliorate and/or prevent disease, including infection leading to disease. Animals to be treated using a therapeutic composition of the present invention include any animal that can be infected by an infectious agent that is susceptible to inhibition of dibasic amino acid processing endoprotease activity or any animal that is producing too much or too little of a protein that requires a dibasic amino acid processing endoprotease for maturation. Preferred animals to treat include mammals, birds, fish, amphibians and insects, with humans, livestock and pets being more preferred. Even more preferred are humans, apes, cats, dogs, cattle, horses, monkeys, swine and sheep with humans being particularly preferred.

Therapeutic compositions of the present invention can be administered by a variety of routes appreciated by those skilled in the art, and can vary depending on the form of the composition. Examples of routes to administer a therapeutic composition of the present invention include, but are not limited to, aural, bronchial, genital, inhalatory, nasal, ocular, oral, parenteral, rectal, topical, transdermal and urethral routes. Aural delivery can include ear drops, nasal delivery can include nose drops and ocular delivery can include eye drops. Oral delivery can include solids and liquids that can be taken through the mouth. Parenteral delivery can include intradermal, intramuscular, intraperitoneal, intrapleural, intrapulmonary, intravenous, subcutaneous, atrial catheter and venal catheter routes.

Methods to prepare and administer compositions via these routes are well known to those skilled in the art. Compositions of the present invention are administered in an effective manner which depends on the use of the composition. For example, in order to protect an animal from disease, a composition of the present invention is administered to the animal in an effective manner such that the composition is capable of protecting that animal from that disease. Compositions of the present invention can be administered to animals prior to disease in order to prevent disease and/or can be administered to animals after onset of the disease in order to treat the disease. Acceptable protocols to administer compositions in an effective manner include individual dose size, number of doses, frequency of dose administration, and mode of administration. Determination of such protocols can be accomplished by those skilled in the art.

The following examples are provided for the purposes of illustration and are not intended to limit the scope of the present invention. Standard techniques (e.g., recombinant DNA and culturing techniques) referred to in the examples are disclosed in a variety of references including, for example, Sambrook et al., ibid. and/or Guthrie et al. (eds.), 1991, *Methods in Enzymology* 194, Academic Press, San Diego.

EXAMPLES

Example 1

This Example describes the cloning and sequencing of a nucleic acid molecule of the present invention.

A nucleic acid molecule of about 483 nucleotides, denoted nhTCP$_{483}$, representing a partial human TCP gene, was isolated from human CD4+ T-lymphocyte polyA+ RNA in the following manner. Total RNA was extracted from human CD4+ T-lymphocyte CEM cells (available from American Type Culture Collection (ATCC), Rockville, Md.) and poly A+ RNA was separated from total RNA by oligo-dT cellulose chromatography using standard techniques. A first strand cDNA product was produced by incubating, under standard reverse transcription conditions, the polyA+ RNA and a degenerate primer having SEQ ID NO:7, namely 5' TCCCGTCGACHYCCCABSWRTGRRYDGW-CATGAA 3' (H is a mixture of A, T, and C; Y is a mixture of T and C; B is a mixture of G, T and C; S is a mixture of G and C; W is a mixture of A and T; R is a mixture of A and G; and D is a mixture of G, A and T).

Nucleic acid molecule nhTCP$_{483}$ was PCR amplified from the cDNA product using standard protocols and the following primers: a degenerate "sense" primer having SEQ ID NO:8, namely 5' TGTCGGATCCTGYGGNGTHGGH-GTDGCHTAYAAYKCC 3' (K is a mixture of G and T); and a degenerate "antisense" primer having SEQ ID NO:9, namely 5' TCCCGTCGACSGGDGCWGMDGCH-GAKGTSCCHGWRTG 3' (M is a mixture of A and C). The primers were designed from related protease sequences, particularly using the most conserved sequences shared by all known subtilisin-like enzymes and biased toward human gene sequences, and were intended to amplify a nucleic acid molecule comprising most, if not all, of the catalytic site. However, due to the high degeneracy required in designing primers, a number of primers needed to be tested in order to accomplish a successful amplification, requiring several iterations of design of appropriate primers. Of 8 primers tested, only 2 gave the correct product.

The amplified PCR fragment was recovered and submitted to standard DNA sequencing techniques. An about 483 nucleotide sequence of nhTCP$_{483}$ was determined and is presented as SEQ ID NO:1. SEQ ID NO:1 apparently encodes a protein of about 161 amino acids, which is presented as SEQ ID NO:2. Neither the translation initiation site of the protein nor the translation termination codon is contained within this nucleic acid molecule.

Comparison of the deduced nucleic acid sequence of nhTCP$_{483}$ (i.e., SEQ ID NO:1) with the nucleic acid sequence of the genes encoding human furin (hFUR), human PC1 (hPC1), human PC2 (hPC2), human PC4 (hPC4), mouse PC5 (mPC5) and rat PC5 (rPC5) indicated that SEQ ID NO:1 was about 70%, 66.7%, 57.7%, 63.7% and 85% identical to the corresponding region of the respective genes. The deduced amino acid sequence SEQ ID NO:2 was about 71.6%, 66.1%, 56.4%, 73.5% and 95.1% identical to the respective corresponding regions of hFUR, hPC1, hPC2, hPC4, mPC5 and rPC5.

Example 2

This Example describes the cloning and sequencing of another nucleic acid molecule of the present invention.

A nucleic acid molecule of about 2400 nucleotides, denoted nhTCP$_{-2400}$, representing a partial human TCP gene, was PCR amplified from the cDNA product described in Example 1 using standard protocols and the following primers: a degenerate "sense" primer having SEQ ID NO:10, namely 5' CCAAGYATGTGGTAYATGCAYTGY-AGY 3'; and a degenerate "antisense" primer having SEQ ID NO:11, namely 5' GGCTGCTCAGCCTTGGAATGTA-CATGTTTT 3'. The primers were designed using mouse and rat PC5 gene sequences. The antisense primer spans the translation stop codon of the mouse and rat PC5 genes.

The amplified PCR fragment was recovered and submitted to standard DNA sequencing techniques. An about 111 nucleotide sequence of the 5' end of nhTCP$_{-2400}$ was determined and is presented as SEQ ID NO:3. SEQ ID NO:4 apparently encodes the first 37 amino acids of hTCP$_{-800}$ and is presented as SEQ ID NO:4.

Comparison of SEQ ID NO:2 and SEQ ID NO:4 with mouse and rat PC5 proteins indicates that SEQ ID NO:4 is amino terminal to SEQ ID NO:2 and that SEQ ID NO:4 as well as SEQ ID NO:2 contain portions of the catalytic domain.

Comparison of SEQ ID NO:3 with the sequences of the genes encoding rPC5 and mPC5 indicates that SEQ ID NO:3 is about 91.9% identical with the corresponding regions of the rat and mouse genes. The amino acid sequences of the three proteins in that region are identical. When compared with the mature rPC5 and mPC5 proteins, the amino terminus of the protein encoded by nhTCP$_{-2400}$ lacks only about the first 17 amino acids of the corresponding region of the mature rPC5 and mPC5 proteins.

Additional nucleic sequence analysis of nhTCP$_{-2400}$ yielded two nucleic acid sequences: (a) an 918 nucleotide sequence at the 5' end of nhTCP$_{-2400}$, referred to herein as SEQ ID NO:12, which encodes an amino acid sequence of 306 amino acids, referred to herein as SEQ ID NO:13; and (b) an 867 nucleotide sequence at the 3' end of nhTCP$_{-2400}$ (including the stop codon), referred to herein as SEQ ID NO:14, which encodes an amino acid sequence of 288 amino acids, referred to herein as SEQ ID NO:15. SEQ ID NO:12 includes both SEQ ID NO:1 and SEQ ID NO:3 in that SEQ ID NO:1 begins at nucleotide position 280 of SEQ ID NO:12, and SEQ ID NO:3 begins at nucleotide position 16 of SEQ ID NO:12. At certain positions in SEQ ID NO:12 and in SEQ ID NO:14, the nucleotide was not identified and is denoted "N".

In order to compare the nucleotide and amino acid sequences with those of mouse PC5, the "N"s were changed to "A"s. Comparison of SEQ ID NO:12 and SEQ ID NO:14 with the corresponding regions of the mouse PC5 gene indicated that the human gene shares about 85% nucleic acid sequence identity with the corresponding regions of the mouse gene. Comparison of SEQ ID NO:13 with the corresponding region of mouse PC5 indicated that SEQ ID NO:13 was about 99% identical to the corresponding region of the mouse protein. Comparison of SEQ ID NO:15 with the corresponding regions of mouse PC5 indicated that SEQ ID NO:15 was about 88% identical to the corresponding region of the mouse protein.

Example 3

This Example demonstrates that a gene including nhTCP$_{483}$ is transcribed in human CD4+ T-lymphocytes as well as in a human colon carcinoma line.

Total and polyA+ RNA was isolated from human CD4+ T-lymphocyte CEM and H9 (available from ATCC) cell lines and from human colon carcinoma LoVo cells (also available from ATCC) using standard procedures. The RNA populations were submitted to Northern blot analysis according to standard procedures and were probed with the labelled nucleic acid molecule nhTCP$_{483}$. The probe hybridized with RNA species of about 3.5 kb and about 6 kb in all cell lines. The RNA species of about 3.5 kb is of a size expected to encode a protein having a size similar to that of mouse or rat PC5. The identity of the larger molecular weight species is as yet unknown, but it should be noted that a larger molecular weight RNA is also found in similar experiments using mouse or rat PC5 gene probes.

A similar experiment in which a probe corresponding to the human furin gene was used in Northern analysis of RNA isolated from each of the three cell lines indicated that furin is also expressed by each of these cell lines. It is of interest that even though these cell lines produce furin, another enzyme, namely hTCP, is also produced, suggesting the latter's distinct role in processing proteins having dibasic amino acid processing sites, such as being able to function in a particular cellular compartment and/or to cleave a particular substrate, such as has been found for the processing of the multivalent precursor protein propiomelanocortin which is cleaved by PC1 and PC2 at distinct sites within the molecule (see Zhou et al., 1993, *J. Biol. Chem.* 268, 1763–1769).

Example 4

This Example describes the production of certain recombinant molecules and recombinant cells of the present invention.

Recombinant molecule p$\alpha$/nhTCP$_{-2400}$ is prepared as follows. Nucleic acid molecule nhTCP$_{-2400}$, produced as described in Example 1, is ligated to a nucleic acid sequence encoding a *S. cerevisiae* $\alpha$-factor signal segment to form an $\alpha$-signal/nhTCP$_{-2400}$ fragment, denoted herein as $\alpha$/nhTCP$_{-2400}$. The $\alpha$/nhTCP$_{-2400}$ fusion gene is operatively linked to a *S. cerevisiae* ADH2/GAPDH promoter and CYC1 transcription termination sequences and joined with other yeast shuttle expression vector sequences to form recombinant molecule p$\alpha$/nhTCP$_{-2400}$. Recombinant molecule p$\alpha$/nhTCP$_{-2400}$ contains yeast (2$\mu$) and bacterial replication control sequences as well as a bacterial gene encoding ampicillin resistance (Amp), and auxotrophic leu2-d and prototrophic URA3 yeast genes.

Recombinant molecule p$\alpha$/nhTCP$_{-2400}$ is transformed into *S. cerevisiae* CB023, a cir° strain that is disclosed in Brenner et al., 1992, *Proc. Natl. Acad. Sci.* 89, 922–926 to form recombinant cell *S. cerevisiae* CB023:p$\alpha$/nhTCP$_{-2400}$.

Recombinant molecule p$\alpha$/nhTCP is produced in a similar manner to recombinant molecule p$\alpha$/nhTCP$_{-2400}$ except that the entire coding region of hTCP is included in the recombinant molecule. Recombinant cell *S. cerevisiae* CB023:p$\alpha$/nhTCP is produced by introducing recombinant molecule p$\alpha$/nhTCP into *S. cerevisiae* CB023.

Culturing of recombinant cells *S. cerevisiae* CB023:p$\alpha$/nhTCP$_{-2400}$ and *S. cerevisiae* CB023:p$\alpha$/nhTCP under appropriate conditions leads to the production of TCP proteins of the present invention.

Example 5

This Example describes the production of another recombinant molecule and recombinant cell of the present invention. Such a recombinant cell can be used to identify inhibitors of HIV gp160 cleavage.

Recombinant molecule p$\alpha$/env (also denoted pBS8) that includes the gene encoding HIV-1$_{SF2}$ gp160, was produced as described in Example 1 of Ser. No. 08/088,322, ibid. Briefly, the envelope (env) gene encoding the gp160 precursor envelope protein (about 825 amino acids) of HIV-1$_{SF2}$ (Sanchez-Pescador et al., 1985, *Science* 227, 484–492) was ligated to a nucleic acid sequence encoding an $\alpha$-factor signal and leader segment of about 86 amino acids to form an $\alpha$-leader/env-gene fragment ($\alpha$/env) in which the signal sequence of the env gene was replaced by the $\alpha$-factor signal and leader sequences in a manner similar to the method by which the epidermal growth factor gene was joined to $\alpha$-factor signal and leader sequences in Brake et al., 1984, *Proc. Natl. Acad. Sci.* 81, 4642–4646. The $\alpha$-factor segment, also denoted $\alpha$-F leader, also included a dibasic amino acid processing site at its carboxyl terminus. The $\alpha$/env fusion gene was operatively linked to a *S. cerevisiae* ADH2/GAPDH promoter and $\alpha$-factor transcription termination sequences and joined with other yeast shuttle expression vector sequences to form recombinant molecule p$\alpha$/env, also denoted pBS8. Recombinant molecule p$\alpha$/env contains yeast (2$\mu$) and bacterial replication control sequences as well as a bacterial gene encoding ampicillin resistance (Amp), and auxotrophic leu2-d and prototrophic URA3 yeast genes.

Recombinant molecules p$\alpha$/env and p$\alpha$/nhTCP, produced as described in Example 5, are transformed into a *S. cerevisiae* Kex2 endoprotease-deficient strain, called *S. cerevisiae* kex2$\Delta$, which has the genotype pep4::URA3 kex2::TRP1 prb leu2 his4 ura3 trp1 and was produced as described in Example 3 of Ser. No. 08/088,322, ibid. The transformed strain, denoted *S. cerevisiae* kex2$\Delta$:p$\alpha$/env,p$\alpha$/nhTCP is cultured under conditions suitable to produce gp160 and hTCP. The ability of hTCP to cleave gp160 into gp120 and gp41 is demonstrated using immunoprecipitation and immunoblot techniques similar to those disclosed in Example 1 of Ser. No. 08/088,322, ibid. The ability of *S. cerevisiae* kex2$\Delta$:p$\alpha$/env,p$\alpha$/nhTCP to express gp120 and gp41 on its cell surface is demonstrated using a cell surface biotinylation assay similar to that described in Example 1 of Ser. No. 08/088,322, ibid.

Example 6

This example demonstrates the ability to identify inhibitors of HIV-1 infection using a Kex2 endoprotease-deficient *S. cerevisiae* strain transformed with a gene encoding the human CD4+ T-lymphocyte dibasic amino acid processing endoprotease that can cleave HIV-1 gp160 precursor proteins.

*S. cerevisiae* kex2$\Delta$:p$\alpha$/env,p$\alpha$/nhTCP, produced as described in Example 5, is cultured according to standard techniques (see, for example, Guthrie et al. (eds.), ibid.) and divided into samples that are placed, for example, in microtiter dish wells. Each sample is incubated with about 300 $\mu$M, 100 $\mu$M, 10 $\mu$M, 1 $\mu$M, 300 nM, 100 nM, 10 nM, 1 nM, or none of one of the following peptides: Boc-Arg-Glu-Lys-Arg-MCA or Boc-Gln-Arg-Arg-MCA under culturing conditions for about 12 hours. Putative inhibitory compounds can be pre-incubated with the yeast strain prior to induction of gp160 expression. After culturing, cells from each sample are lysed and submitted to immunoprecipitation and/or immunoblot analysis to measure gp160, gp120, and gp41 production, using the techniques described in Example 5. Peptides that inhibit cleavage of gp160 to gp120 at suitable doses are identified and can be further tested for their ability to inhibit syncytium and/or infectious virus formation by HIV-1-infected CD4+ T-lymphocytes, using techniques such as those disclosed herein and in Ser. No. 08/088,322, ibid.

What is claimed is:

1. An isolated nucleic acid molecule comprising a dibasic amino acid processing endoprotease gene nhTCP and nucleic acid molecules comprising fragments thereof that encode a dibasic amino acid processing endoprotease having proteolytic activity.

2. The nucleic acid molecule of claim 1, wherein said nucleic acid molecule comprises a nucleic acid sequence that encodes a protein capable of cleaving a precursor envelope protein of a virus that infects a cell expressing a CD4+ cell marker on the surface of said cell.

3. The nucleic acid molecule of claim 2, wherein said virus is selected from the group consisting of a lentivirus and a lymphotropic virus.

4. The nucleic acid molecule of claim 2, wherein said virus is capable of infecting an animal selected from the group consisting of humans, apes, cats, dogs, cattle, horses, swine, sheep and monkeys.

5. The nucleic acid molecule of claim 1, wherein said nucleic acid molecule comprises a nucleic acid molecule selected from the group consisting of $nhTCP_{\sim 2400}$ and nhTCP.

6. The nucleic acid molecule of claim 1, wherein said nucleic acid encodes a protein that is used to identify an inhibitory compound that reduces the infectivity of an infectious agent susceptible to inhibition of dibasic amino acid processing endoprotease activity.

7. A recombinant molecule comprising an isolated nucleic acid molecule as set forth in claim 1 operatively linked to a transcription control sequence.

8. A recombinant cell comprising a cell having an isolated nucleic acid molecule as set forth in claim 1.

9. An isolated nucleic acid molecule selected from the group consisting of a nucleic acid molecule comprising a nucleic acid sequence having at least about 86 percent nucleic acid sequence identity with SEQ ID NO:1, a nucleic acid molecule comprising a nucleic acid sequence having at least about 93 percent nucleic acid sequence identity with SEQ ID NO:3, a nucleic acid molecule comprising a nucleic acid sequence having at least about 86 percent nucleic acid sequence identity with SEQ ID NO:12 and a nucleic acid molecule comprising a nucleic acid sequence having at least about 86 percent nucleic acid sequence identity with SEQ ID NO:14.

10. The nucleic acid molecule of claim 9, wherein said nucleic acid molecule comprises a nucleic acid sequence that encodes a human CD4+ T-lymphocyte dibasic amino acid processing endoprotease protein.

11. The nucleic acid molecule of claim 9, wherein said nucleic acid molecule comprises a nucleic acid sequence that encodes a protein having dibasic amino acid processing endoprotease activity.

12. The nucleic acid molecule of claim 9, wherein said nucleic acid molecule comprises a nucleic acid sequence that encodes a protein capable of cleaving a precursor envelope protein of a virus that infects a cell expressing a CD4+ cell marker on the surface of said cell.

13. The nucleic acid molecule of claim 9, wherein said nucleic acid molecule comprises a nucleic acid molecule selected from the group consisting of $nhTCP_{483}$, $nhTCP_{\sim 2400}$ and nhTCP.

14. The nucleic acid molecule of claim 9, wherein said nucleic acid molecule comprises an oligonucleotide.

15. The nucleic acid molecule of claim 9, wherein said nucleic acid molecule reduces the infectivity of an infectious agent susceptible to inhibition of dibasic amino acid processing endoprotease activity.

16. The nucleic acid molecule of claim 9, wherein said nucleic acid encodes a protein that is used to identify an inhibitory compound that reduces the infectivity of an infectious agent susceptible to inhibition of dibasic amino acid processing endoprotease activity.

17. A recombinant molecule comprising an isolated nucleic acid molecule as set forth in claim 9 operatively linked to a transcription control sequence.

18. A recombinant cell comprising a cell having an isolated nucleic acid molecule as set forth in claim 9.

19. An isolated nucleic acid molecule comprising a nucleic acid molecule selected from the group consisting of nhTCp483, nhTCP$_{-2400}$ and nhTCP.

20. A recombinant cell comprising a cell transformed with a first nucleic acid molecule capable of hybridizing, under stringent conditions, with a dibasic amino acid processing endoprotease gene comprising nhTCP, wherein said cell is capable of expressing said first nucleic acid molecule.

21. The recombinant cell of claim 20, wherein said cell expresses a precursor protein having a dibasic amino acid processing site.

22. The recombinant cell of claim 21, wherein said precursor protein is encoded by a second nucleic acid molecule that is heterologous to said recombinant cell.

23. The recombinant cell of claim 21, wherein said precursor protein is produced endogenously by said recombinant cell.

24. The recombinant cell of claim 20, wherein said recombinant cell is produced by delivering said first nucleic acid molecule to a host cell in vivo thereby transforming said cell with said first nucleic acid molecule.

25. The recombinant cell of claim 20, wherein said recombinant cell is produced by delivering said first nucleic acid molecule to a host cell in vitro, thereby transforming said cell with said first nucleic acid molecule.

26. The recombinant cell of claim 20, wherein said first nucleic acid molecule encodes a protein having dibasic amino acid processing endoprotease activity.

27. The recombinant cell of claim 20, wherein expression of said first nucleic acid molecule reduces dibasic amino acid processing endoprotease activity in said cell compared to an untransformed cell.

* * * * *

UNITED STATES PATENT AND TRADEMARK OFFICE
CERTIFICATE OF CORRECTION

PATENT NO. : 5,691,183
DATED : November 25, 1997
INVENTOR(S) : Franzusoff et al.

It is certified that error appears in the above-identified patent and that said Letters Patent is hereby corrected as shown below:

In Claim 19, line 3, delete "nhTCp483" and insert -- $nhTCP_{483}$ -- therefor.

Signed and Sealed this

Third Day of March, 1998

BRUCE LEHMAN

Attest:

Attesting Officer

Commissioner of Patents and Trademarks